United States Patent
Van Der Woning et al.

(10) Patent No.: US 12,071,486 B2
(45) Date of Patent: Aug. 27, 2024

(54) BISPECIFIC ANTIGEN BINDING CONSTRUCT

(71) Applicant: argenx BV, Zwijnaarde (BE)

(72) Inventors: Sebastian Van Der Woning, Bachte-Maria-Leerne (BE); Christophe Blanchetot, Destelbergen (BE)

(73) Assignee: argenx BV, Ghent (BE)

( * ) Notice: Subject to any disclaimer, the term of this patent is extended or adjusted under 35 U.S.C. 154(b) by 293 days.

(21) Appl. No.: 16/230,326

(22) Filed: Dec. 21, 2018

(65) Prior Publication Data

US 2019/0218310 A1 Jul. 18, 2019

Related U.S. Application Data

(60) Provisional application No. 62/609,523, filed on Dec. 22, 2017.

(51) Int. Cl.
*C07K 16/46* (2006.01)
*C07K 16/00* (2006.01)

(52) U.S. Cl.
CPC ........ *C07K 16/468* (2013.01); *C07K 2317/22* (2013.01); *C07K 2317/31* (2013.01); *C07K 2317/52* (2013.01); *C07K 2317/526* (2013.01); *C07K 2317/55* (2013.01); *C07K 2317/569* (2013.01); *C07K 2317/64* (2013.01); *C07K 2317/76* (2013.01); *C07K 2317/92* (2013.01)

(58) Field of Classification Search
CPC .............. C07K 16/468; C07K 2317/31; C07K 2317/22; C07K 2317/55; C07K 2317/569; C07K 2317/52; C07K 2317/64
See application file for complete search history.

(56) References Cited

U.S. PATENT DOCUMENTS

| | | | |
|---|---|---|---|
| 5,821,333 A | 10/1998 | Carter et al. | |
| 5,892,019 A | 4/1999 | Schlom et al. | |
| 6,670,453 B2 | 12/2003 | Frenken et al. | |
| 8,216,805 B2 | 7/2012 | Carter et al. | |
| 8,524,231 B2 | 9/2013 | Dreier et al. | |
| 8,629,246 B2 | 1/2014 | Humphreys et al. | |
| 8,703,131 B2 | 4/2014 | Beirnaert et al. | |
| 9,212,230 B2 | 12/2015 | Schuurman et al. | |
| 9,499,634 B2 | 11/2016 | Dixit et al. | |
| 9,834,615 B2 | 12/2017 | Fischer et al. | |
| 2004/0253638 A1 | 12/2004 | Casterman et al. | |
| 2006/0063921 A1 | 3/2006 | Moulder et al. | |
| 2009/0252729 A1 | 10/2009 | Farrington et al. | |
| 2010/0254989 A1 | 10/2010 | Bossenmaier et al. | |
| 2010/0331527 A1 | 12/2010 | Davis et al. | |
| 2011/0081345 A1 | 4/2011 | Moore et al. | |
| 2011/0165621 A1* | 7/2011 | Dreier ................. | C07K 16/467 435/69.6 |
| 2011/0293613 A1 | 12/2011 | Brinkmann et al. | |
| 2012/0184716 A1 | 7/2012 | Fischer et al. | |
| 2013/0178605 A1 | 7/2013 | Blein et al. | |
| 2014/0079689 A1* | 3/2014 | Elliott .................. | C07K 16/247 424/133.1 |
| 2014/0154254 A1 | 6/2014 | Kannan et al. | |
| 2014/0302037 A1 | 10/2014 | Borges et al. | |
| 2014/0363426 A1* | 12/2014 | Moore ............... | C07K 16/2809 424/133.1 |
| 2015/0252119 A1 | 9/2015 | Frey et al. | |
| 2015/0307628 A1 | 10/2015 | Yong et al. | |
| 2016/0017057 A1 | 1/2016 | Emma et al. | |
| 2016/0115241 A1 | 4/2016 | Wei et al. | |
| 2016/0251440 A1 | 9/2016 | Roonbrouck et al. | |
| 2016/0280795 A1* | 9/2016 | Wang ..................... | A61P 35/00 |
| 2016/0319036 A1 | 11/2016 | Bruenker et al. | |
| 2017/0066843 A1 | 3/2017 | Andrey et al. | |
| 2017/0320967 A1 | 11/2017 | Zhi-Yong et al. | |

FOREIGN PATENT DOCUMENTS

| | | |
|---|---|---|
| WO | 2010035012 A1 | 4/2010 |
| WO | 2013064701 A2 | 5/2013 |
| WO | 2013136186 A2 | 9/2013 |
| WO | 2014022540 A1 | 2/2014 |
| WO | 2014124326 A1 | 8/2014 |
| WO | 2015033223 A2 | 3/2015 |
| WO | 2016086186 A2 | 6/2016 |
| WO | 2016086189 A2 | 6/2016 |
| WO | 2016118742 A1 | 7/2016 |
| WO | 2017218707 A2 | 12/2017 |

(Continued)

OTHER PUBLICATIONS

Kontermann, Dual targeting strategies with bispecific antibodies, mAbs, 4(2)182-197 (Year: 2012).*

Brinkmann et al., The making of bispecific antibodies, MABS, 2017, 9(2): 182-212.*

Borrock, et al., (2012) "Revisiting the role of glycosylation in the structure of human lgG Fc," ACS Chem. Biol., 7:1596-1602.

Carter, et al., (2001) "Bispecific human IgG by design," Journal of Immunological Methods, 248:7-15.

Chan, et al., (2010) "Therapeutic antibodies for autoimmunity and inflammation," Nature Reviews Immunology, 10:301-316.

Gunasekaran, et al., (2010) "Enhancing antibody Fc heterodimer formation through electrostatic steering effects," The Journal of Biological Chemistry, 285(25):19637-19646.

Hamers-Casterman, et al., (1993) "Naturally occurring antibodies devoid of light chains," Nature, 363:446-448.

(Continued)

*Primary Examiner* — Hong Sang

(74) *Attorney, Agent, or Firm* — Dechert LLP; Andrew T. Wilkins

(57) ABSTRACT

The present invention relates to bispecific and other multi-specific antigen binding constructs. In certain aspects, the invention relates to bispecific antigen binding constructs comprising a single domain antibody (VHH) antigen binding region fused to an IgG Fc domain; a heavy chain-Fc domain portion of a conventional IgG antibody, and a light chain portion of a conventional IgG antibody. The bispecific antigen binding constructs of the invention are capable of targeting two different antigens separately or in a protein complex.

4 Claims, 12 Drawing Sheets

Specification includes a Sequence Listing.

(56) References Cited

FOREIGN PATENT DOCUMENTS

| | | |
|---|---|---|
| WO | 2018014260 A1 | 1/2018 |
| WO | 2018014855 A1 | 1/2018 |

OTHER PUBLICATIONS

Hinton, et al., (2006) "An engineered human IgG1 antibody with longer serum half-life," The Journal of Immunology, 176:346-356.

International Search Report with Written Opinion for International Application No. PCT/EP2018/086755, dated Mar. 3, 2019.

Klein, et al., (2012) "Progress in overcoming the chain association issue in bispecific heterdimeric IgG antibodies," mAbs, 4(6):653-663.

Labrijn, et al., (2013) "Efficient generation of stable bispecific IgG1 by controlled Fab-arm exchange," PNAS, 110 (13):5145-5150.

Lewis, et al., (2014) "Generation bispecific IgG antibodies by structure-based design of an orthogonal Fab interface," Nature Biotechnology, 32(2):191-198.

Lindhofer, et al., (1995) "Preferential species-restricted heavy/light chain pairing in rat/mouse quadromas," The Journal of Immunology, 155:219-225.

Morea, et al., (2000) "Antibody modeling: Implications for engineering and design," Methods, 20:267-279.

Muda, et al., (2011) "Therapeutic assessment of SEED: a new engineered antibody platform designed to generate mon-and bispecific antibodies," Protein Engineering, Design and Selection, 24(5):447-454.

Presta et al. (2012) "Molecular engineering and design of therapeutic antibodies," Current Opinion in Immunology, 20:460-470.

Ridgway, et al., (1996) "'Knobs-into-holes' engineering of antibody Ch3 domains for heavy chain heterodimerization," Protein Engineering, 9(7):617-621.

Spiess, et al., (2013) "Bispecific antibodies with natural architecture produced by co-culture of bacteria expressing two distinct half-antibodies," Nature Biotechnology, 31(8):753-758.

Vaccaro, et al., "Engineering the Fc region of immunoglobulin G to modulate in vivo antibody levels," Nature Biotechnology, 23(10):1283-1288.

Wang, et al., "Antibody structure, instability, and formulation," Journal of Pharmaceutical Sciences, 96(1):1-26.

Wranik, et al., "LUZ-Y, a novel platform for the mammalian cell production of full-length IgG-bispecific antibodies," The Journal of Biological Chemistry, 287(52):43331-43339.

Yeung, et al., (2009) "Enigeering human IgG1 affinity to human neonatal Fc receptor: Impact of affinity improvement on pharmacokinetics in primates," The Journal of Immunology, 182:7663-7671.

Zalevsky et al. (2010) "Enhanced antibody half-life improves in vivo activity," Nat. Biotechnol., 28(2):157-159.

Bannas et al., "Nanobodies and Nanobody-Based Human Heavy Chain Antibodies As Antitumor Therapeutics," Front Immunol. 2017 1603. doi: 10.3389/fimmu.2017.01603. PMID: 29213270; PMCID: PMC5702627.

* cited by examiner

Figure 4

```
mIgG2aHole              RLNGTAATMGWSCIILFLVATATGVHSGDANPSLEFRLAKTTAPSVYPLA    050
mIgG2aKnob              RLNGTAATMGWSCIILFLVATATGVHSGDANPSLEFRLAKTTAPSVYPLA    050
mFcFusionIgG2aHole      RLNGTAATMGWSCIILFLVATATGVHSGDANPSLEFRL-----------    038
mFcFusionIgG2aKnob      RLNGTAATMGWSCIILFLVATATGVHSGDANPSLEFRL-----------    038
pUPEX36-mIgG2.P9        SLNGTAATMGWSCIILFLVATATGVHSGDASLTLEFRLAKTTAPSVYPLA    050 mIgG2aHole              PVCGDTTGSSVTLGCLVKGYFPEPVTLTWNSGSLSSGVHTFPAVLQSDLY    100
mIgG2aKnob              PVCGDTTGSSVTLGCLVKGYFPEPVTLTWNSGSLSSGVHTFPAVLQSDLY    100
mFcFusionIgG2aHole      --------------------------------------------------
mFcFusionIgG2aKnob      --------------------------------------------------
pUPEX36-mIgG2.P9        PVCGDTTGSSVTLGCLVKGYFPEPVTLTWNSGSLSSGVHTFPAVLQSDLY    100 mIgG2aHole              TLSSSVTVTSSTWPSQSITCNVAHPASSTKVDKKIEPRGPTIKPCPPCKC    150
mIgG2aKnob              TLSSSVTVTSSTWPSQSITCNVAHPASSTKVDKKIEPRGPTIKPCPPCKC    150
mFcFusionIgG2aHole      ---------------------------------EPRGPTIKPCPPCKC    53
mFcFusionIgG2aKnob      ---------------------------------EPRGPTIKPCPPCKC    53
pUPEX36-mIgG2.P9        TLSSSVTVTSSTWPSQSITCNVAHPASSTKVDKKIEPRGPTIKPCPPCKC    150 mIgG2aHole              PAPNLLGGPDVFIFPPKIKDVLMISLSPIVTCVVVDVSEDDPDVQISWFV    200
mIgG2aKnob              PAPNLLGGPDVFIFPPKIKDVLMISLSPIVTCVVVDVSEDDPDVQISWFV    200
mFcFusionIgG2aHole      PAPNLLGGPDVFIFPPKIKDVLMISLSPIVTCVVVDVSEDDPDVQISWFV    103
mFcFusionIgG2aKnob      PAPNLLGGPDVFIFPPKIKDVLMISLSPIVTCVVVDVSEDDPDVQISWFV    103
pUPEX36-mIgG2.P9        PAPNLLGGPSVFIFPPKIKDVLMISLSPIVTCVVVDVSEDDPDVQISWFV    200 mIgG2aHole              NNVEVHTAQTQTHREDYQSTLRVVSALPIQHQDWMSGKEFKCKVNNKDLP    250
mIgG2aKnob              NNVEVHTAQTQTHREDYNSTLRVVSALPIQHQDWMSGKEFKCKVNNKDLP    250
mFcFusionIgG2aHole      NNVEVHTAQTQTHREDYNSTLRVVSALPIQHQDWMSGKEFKCKVNNKDLP    153
mFcFusionIgG2aKnob      NNVEVHTAQTQTHREDYNSTLRVVSALPIQHQDWMSGKEFKCKVNNKDLP    153
pUPEX36-mIgG2.P9        NNVEVHTAQTQTHREDYNSTLRVVSALPIQHQDWMSGKEFKCKVNNKDLP    250
```

Figure 4 (continued)

| | | |
|---|---|---|
| mIgG2aHole | APEERTISKPKGSVRAPQVYVLPPPEEEMTKKQVTLSCAVTDFMPEDIYV | 300 |
| mIgG2aKnob | APEERTISKPKGSVRAPQVYVLPPPEEEMTKKQVTLWCMVTDFMPEDIYV | 300 |
| mFcFusionIgG2aHole | APEERTISKPKGSVRAPQVYVLPPPEEEMTKKQVTLSCAVTDFMPEDIYV | 203 |
| mFcFusionIgG2aKnob | APEERTISKPKGSVRAPQVYVLPPPEEEMTKKQVTLWCMVTDFMPEDIYV | 203 |
| pUPEX36-mIgG2.P9 | APIERTISKPKGSVRAPQVYVLPPPEEEMTKKQVTLTCMVTDFMPEDIYV | 300 |
| mIgG2aHole | EWTNNGKTELNYKNTEPVLDSDGSYFMVSKLRVEKKNWVERNSYSCSVVH | 350 |
| mIgG2aKnob | EWTNNGKTELNYKNTEPVLDSDGSYFMYSKLRVEKKNWVERNSYSCSVVH | 350 |
| mFcFusionIgG2aHole | EWTNNGKTELNYKNTEPVLDSDGSYFMVSKLRVEKKNWVERNSYSCSVVH | 253 |
| mFcFusionIgG2aKnob | EWTNNGKTELNYKNTEPVLDSDGSYFMYSKLRVEKKNWVERNSYSCSVVH | 253 |
| pUPEX36-mIgG2.P9 | EWTNNGKTELNYKNTEPVLDSDGSYFMYSK--------------- | 330 |
| mIgG2aHole | EGLHNHHTTKSFSRTPGK**SRAAA | 373 |
| mIgG2aKnob | EGLHNHHTTKSFSRTPGK**SRAAA | 373 |
| mFcFusionIgG2aHole | EGLHNHHTTKSFSRTPGK**SRAAA | 276 |
| mFcFusionIgG2aKnob | EGLHNHHTTKSFSRTPGK**SRAAA | 276 |
| pUPEX36-mIgG2.P9 | ------------------------- | |

730RU coating of Target A

624RU coating of Target B

579RU coating of Target A and Target B complex

SEQUENCE LISTING

<160> NUMBER OF SEQ ID NOS: 36

<210> SEQ ID NO 1
<211> LENGTH: 10
<212> TYPE: PRT
<213> ORGANISM: Homo sapiens

<400> SEQUENCE: 1

Glu Pro Lys Ser Cys Asp Lys Thr His Thr
1               5                  10

<210> SEQ ID NO 2
<211> LENGTH: 5
<212> TYPE: PRT
<213> ORGANISM: Homo sapiens

<400> SEQUENCE: 2

Cys Pro Pro Cys Pro
1               5

<210> SEQ ID NO 3
<211> LENGTH: 8
<212> TYPE: PRT
<213> ORGANISM: Homo sapiens

<400> SEQUENCE: 3

Ala Pro Glu Leu Leu Gly Gly Pro
1               5

<210> SEQ ID NO 4
<211> LENGTH: 10
<212> TYPE: PRT
<213> ORGANISM: Homo sapiens

<400> SEQUENCE: 4

Cys Cys Val Glu Cys Pro Pro Cys Pro
1               5                  10

<210> SEQ ID NO 5
<211> LENGTH: 7
<212> TYPE: PRT
<213> ORGANISM: Homo sapiens

<400> SEQUENCE: 5

Ala Pro Pro Val Ala Gly Pro
1               5

<210> SEQ ID NO 6
<211> LENGTH: 12
<212> TYPE: PRT
<213> ORGANISM: Homo sapiens

<400> SEQUENCE: 6

Glu Leu Lys Thr Pro Leu Gly Asp Thr Thr His Thr
1               5                  10

<210> SEQ ID NO 7
<211> LENGTH: 50
<212> TYPE: PRT
<213> ORGANISM: Homo sapiens

<400> SEQUENCE: 7

Cys Pro Arg Cys Pro Glu Pro Lys Ser Cys Asp Thr Pro Pro Cys
1               5                  10                 15

Pro Arg Cys Pro Glu Pro Lys Ser Cys Asp Thr Pro Pro Cys Pro
            20                  25                 30

Arg Cys Pro Glu Pro Lys Ser Cys Asp Thr Pro Pro Cys Pro Arg
        35                  40                 45

Cys Pro

<210> SEQ ID NO 8
<211> LENGTH: 7
<212> TYPE: PRT
<213> ORGANISM: Homo sapiens

<400> SEQUENCE: 8

Glu Ser Lys Tyr Gly Pro Pro
1               5

<210> SEQ ID NO 9
<211> LENGTH: 5
<212> TYPE: PRT
<213> ORGANISM: Homo sapiens

<400> SEQUENCE: 9

Cys Pro Ser Cys Pro
1               5

<210> SEQ ID NO 10
<211> LENGTH: 8
<212> TYPE: PRT
<213> ORGANISM: Homo sapiens

<400> SEQUENCE: 10

Ala Pro Glu Phe Leu Gly Gly Pro
1               5

<210> SEQ ID NO 11
<211> LENGTH: 373
<212> TYPE: DNA
<213> ORGANISM: Artificial sequence
<220> FEATURE:
<223> OTHER INFORMATION: Synthetic polynucleotide

<400> SEQUENCE: 11
gagttgcagg tggtggagtc tgggggagga ttggtgcagg ctggggcctc tctgagactc      60
tcctgtgtag cctctggacg caccttcagt agttattcca tggcctggtt ccgccaggct     120
ccagggaagg agcgtgagtt tgtcgcgacg gttagtaatt ggaatgatta catcacaacc     180
tatgcagact ccgtgaaggg ccgattcacc atctccagag acaatgccaa aaacacggtg     240
tctctgcaaa tgaacggcct gaaacctgag gacacggccg tttattactg tgcagcgcgg     300
accggggctc ctagggtcac ttccggacag tatgactact ggggccaggg gacccaggtc     360
accgtgtcct cag                                                        373

<210> SEQ ID NO 12
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 12

Glu Leu Gln Val Val Glu Ser Gly Gly Gly Leu Val Gln Ala Gly Ala
1               5                   10                  15

Ser Leu Arg Leu Ser Cys Val Ala Ser Gly Arg Thr Phe Ser Ser Tyr
            20                  25                  30

Ser Met Ala Trp Phe Arg Gln Ala Pro Gly Lys Glu Arg Glu Phe Val
        35                  40                  45

Ala Thr Val Ser Asn Trp Asn Asp Tyr Ile Thr Thr Tyr Ala Asp Ser

Val Lys Gly Arg Phe Thr Ile Ser Arg Asp Asn Ala Lys Asn Thr Val
65                  70                  75                  80

Ser Leu Gln Met Asn Gly Leu Lys Pro Glu Asp Thr Ala Val Tyr Tyr
                85                  90                  95

Cys Ala Ala Arg Thr Gly Ala Pro Arg Val Thr Ser Gly Gln Tyr Asp
            100                 105                 110

Tyr Trp Gly Gln Gly Thr Gln Val Thr Val Ser Ser
        115                 120

<210> SEQ ID NO 13
<211> LENGTH: 361
<212> TYPE: DNA
<213> ORGANISM: Artificial sequence
<220> FEATURE:
<223> OTHER INFORMATION: Synthetic polynucleotide

<400> SEQUENCE: 13
gagttgcagc tggtggagtc tgggggaggc ttggtgcagc ctggggggtc tcggagactc      60
tcctgtgctg cctctgggtt cacctacagt gactactgga tgtattgggt ccgtcagcct     120
ccagggaagg gactcgagtg gtctcaaat attaattctg aaggtggtag cacagcctat      180
gcagactccg tgaagggccg attcaccatc tccagagaca acgccaagaa cacgctgtat     240
ctgcaaatga acagtctgaa atctgaggac acggccgtat actactgtgt aagagcatta     300
agcagtggtc aatggtaccc ggcctactgg ggccagggga cccaggtcac cgtgtcctcc     360
g                                                                    361

<210> SEQ ID NO 14
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 14

Glu Leu Gln Leu Val Glu Ser Gly Gly Gly Leu Val Gln Pro Gly Gly
1               5                   10                  15

Ser Arg Arg Leu Ser Cys Ala Ala Ser Gly Phe Thr Tyr Ser Asp Tyr
                20                  25                  30

Trp Met Tyr Trp Val Arg Gln Pro Pro Gly Lys Gly Leu Glu Trp Val
            35                  40                  45

Ser Asn Ile Asn Ser Glu Gly Gly Ser Thr Ala Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Val Arg Ala Leu Ser Ser Gly Gln Trp Tyr Pro Ala Tyr Trp Gly Gln
            100                 105                 110

Gly Thr Gln Val Thr Val Ser Ser
        115                 120

<210> SEQ ID NO 15
<211> LENGTH: 796
<212> TYPE: DNA
<213> ORGANISM: Artificial sequence
<220> FEATURE:
<223> OTHER INFORMATION: Synthetic polynucleotide

<400> SEQUENCE: 15

```
ctgtcgtctc actctgagtt gcagctggtg gagtctgggg gaggcttggt gcagcctggg      60
gggtctcgga gactctcctg tgctgcctct gggttcacct acagtgacta ctggatgtat     120
tgggtccgtc agcctccagg gaagggactc gagtgggtct caaatattaa ttctgaaggt     180
ggtagcacag cctatgcaga ctccgtgaag ggccgattca ccatctccag agacaacgcc     240
aagaacacgc tgtatctgca aatgaacagt ctgaaatctg aggacacggc cgtatactac     300
tgtgtaagag cattaagcag tggtcaatgg tacccggcct actggggcca ggggacccag     360
gtcaccgtgt cctccgcctc cgcggccgca agcggtggag gcggttcagg cggaggtgga     420
tctggcggtg gcggaagtgc acaggcaggg ctgactcagc tgccctccgt gtctggatcc     480
ccaggccaga gatcaccat ctcctgcact ggaagcagca gcaacatcag ggttggttat     540
aatgttcagc ggttccagca cctcccagga acaccccccc aactgctcat ctatggtaac     600
agcaatcaag cttcgggggt cccagaccgc ttctctggct ccaagtctgg cagctcggcc     660
tccctgacca tcactgggct ccaggctgag gacgaggctg actattactg tgaatgctat     720
gacagcggcc tcagtgggcc tgtgttcggc ggagggacca agctgaccgt cctcggtgag     780
cctgagacga cacgcc                                                     796
```

<210> SEQ ID NO 16
<211> LENGTH: 260
<212> TYPE: PRT
<213> ORGANISM: Artificial sequence
<220> FEATURE:
<223> OTHER INFORMATION: Synthetic polypeptide

<400> SEQUENCE: 16

```
Glu Leu Gln Leu Val Glu Ser Gly Gly Gly Leu Val Gln Pro Gly Gly
1               5                   10                  15

Ser Arg Arg Leu Ser Cys Ala Ala Ser Gly Phe Thr Tyr Ser Asp Tyr
            20                  25                  30

Trp Met Tyr Trp Val Arg Gln Pro Pro Gly Lys Gly Leu Glu Trp Val
        35                  40                  45

Ser Asn Ile Asn Ser Glu Gly Gly Ser Thr Ala Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Val Arg Ala Leu Ser Ser Gly Gln Trp Tyr Pro Ala Tyr Trp Gly Gln
            100                 105                 110

Gly Thr Gln Val Thr Val Ser Ser Ala Ser Ala Ala Ala Ser Gly Gly
        115                 120                 125

Gly Gly Ser Gly Gly Gly Gly Ser Gly Gly Gly Gly Ser Ala Gln Ala
    130                 135                 140

Gly Leu Thr Gln Leu Pro Ser Val Ser Gly Ser Pro Gly Gln Lys Ile
145                 150                 155                 160

Thr Ile Ser Cys Thr Gly Ser Ser Ser Asn Ile Arg Val Gly Tyr Asn
                165                 170                 175

Val Gln Arg Phe Gln His Leu Pro Gly Thr Pro Pro Gln Leu Leu Ile
            180                 185                 190

Tyr Gly Asn Ser Asn Gln Ala Ser Gly Val Pro Asp Arg Phe Ser Gly
        195                 200                 205
```

Ser Lys Ser Gly Ser Ser Ala Ser Leu Thr Ile Thr Gly Leu Gln Ala
    210                 215                 220

Glu Asp Glu Ala Asp Tyr Tyr Cys Glu Cys Tyr Asp Ser Gly Leu Ser
225                 230                 235                 240

Gly Pro Val Phe Gly Gly Thr Lys Leu Thr Val Leu Gly Glu Pro
                245                 250                 255

Glu Thr Thr Arg
            260

<210> SEQ ID NO 17
<211> LENGTH: 1104
<212> TYPE: DNA
<213> ORGANISM: Artificial sequence
<220> FEATURE:
<223> OTHER INFORMATION: Synthetic polynucleotide

<400> SEQUENCE: 17
cgtttaaacg gtaccgccgc caccatgggc tggtcctgca tcatcctgtt tctggtggcc     60
accgccacag gcgtccactc tggagacgcc aatccttcac tcgaattccg tctcgctaaa    120
acaacagccc catcggtcta tccactggcc cctgtgtgtg agatacaac tggctcctcg    180 gtgactctag gatgcctggt caagggttat ttccctgagc cagtgacctt gacctggaac    240
tctggatccc tgtccagtgg tgtgcacacc ttcccagctg tcctgcagtc tgacctctac    300
accctcagca gctcagtgac tgtaacctcg agcacctggc ccagccagtc catcacctgc    360
aatgtggccc accggcaag cagcaccaag gtggacaaga aaattgagcc cagagggccc     420
acaatcaagc cctgtcctcc atgcaaatgc ccagcaccta acctcttggg tggaccagac    480
gtcttcatct tccctccaaa gatcaaggat gtactcatga tctccctgag ccccatagtc    540
acatgtgtgg tggtggatgt gagcgaggat gacccagatg tccagatcag ctggtttgtg    600
aacaacgtgg aagtacacac agctcagaca caaacccata gagaggatta ccagagtact    660
ctccgggtgg tcagtgccct ccccatccag caccaggact ggatgagtgg caaggagttc    720
aaatgcaagg tcaacaacaa agaccctccca gcgcccgaag agagaaccat ctcaaaaccc    780
aaagggtcag taagagctcc acaggtatat gtcttgcctc caccagaaga agagatgact    840
aagaaacagg tcactctgtc ctgcgctgtc acagacttca tgcctgaaga catttacgtg    900
gagtggacca caacgggaaa acagagcta aactacaaga cactgaacc agtcctggac     960 tctgatggtt cttacttcat ggtgagcaag ctgagagtgg aaaagaagaa ctgggtggaa   1020
agaaatagct actcctgttc agtggtccac gagggtctgc acaatcacca cacgactaag   1080
agcttctccc ggactccggg taaa                                          1104

<210> SEQ ID NO 18
<211> LENGTH: 368
<212> TYPE: PRT
<213> ORGANISM: Artificial sequence
<220> FEATURE:
<223> OTHER INFORMATION: Synthetic polypeptide

<400> SEQUENCE: 18

Arg Leu Asn Gly Thr Ala Ala Thr Met Gly Trp Ser Cys Ile Ile Leu
1               5                   10                  15

Phe Leu Val Ala Thr Ala Thr Gly Val His Ser Gly Asp Ala Asn Pro
                20                  25                  30

Ser Leu Glu Phe Arg Leu Ala Lys Thr Thr Ala Pro Ser Val Tyr Pro
            35                  40                  45

```
Leu Ala Pro Val Cys Gly Asp Thr Thr Gly Ser Ser Val Thr Leu Gly
 50                  55                  60

Cys Leu Val Lys Gly Tyr Phe Pro Glu Pro Val Thr Leu Thr Trp Asn
 65                  70                  75                  80

Ser Gly Ser Leu Ser Ser Gly Val His Thr Phe Pro Ala Val Leu Gln
                 85                  90                  95

Ser Asp Leu Tyr Thr Leu Ser Ser Val Thr Val Thr Ser Ser Thr
                100                 105                 110

Trp Pro Ser Gln Ser Ile Thr Cys Asn Val Ala His Pro Ala Ser Ser
                115                 120                 125

Thr Lys Val Asp Lys Lys Ile Glu Pro Arg Gly Pro Thr Ile Lys Pro
                130                 135                 140

Cys Pro Pro Cys Lys Cys Pro Ala Pro Asn Leu Leu Gly Gly Pro Asp
145                 150                 155                 160

Val Phe Ile Phe Pro Pro Lys Ile Lys Asp Val Leu Met Ile Ser Leu
                165                 170                 175

Ser Pro Ile Val Thr Cys Val Val Asp Val Ser Glu Asp Pro
                180                 185                 190

Asp Val Gln Ile Ser Trp Phe Val Asn Asn Val Glu Val His Thr Ala
                195                 200                 205

Gln Thr Gln Thr His Arg Glu Asp Tyr Gln Ser Thr Leu Arg Val Val
 210                 215                 220

Ser Ala Leu Pro Ile Gln His Gln Asp Trp Met Ser Gly Lys Glu Phe
225                 230                 235                 240

Lys Cys Lys Val Asn Asn Lys Asp Leu Pro Ala Pro Glu Glu Arg Thr
                245                 250                 255

Ile Ser Lys Pro Lys Gly Ser Val Arg Ala Pro Gln Val Tyr Val Leu
                260                 265                 270

Pro Pro Pro Glu Glu Glu Met Thr Lys Lys Gln Val Thr Leu Ser Cys
                275                 280                 285

Ala Val Thr Asp Phe Met Pro Glu Asp Ile Tyr Val Glu Trp Thr Asn
290                 295                 300

Asn Gly Lys Thr Glu Leu Asn Tyr Lys Asn Thr Glu Pro Val Leu Asp
305                 310                 315                 320

Ser Asp Gly Ser Tyr Phe Met Val Ser Lys Leu Arg Val Glu Lys Lys
                325                 330                 335

Asn Trp Val Glu Arg Asn Ser Tyr Ser Cys Ser Val Val His Glu Gly
                340                 345                 350

Leu His Asn His His Thr Thr Lys Ser Phe Ser Arg Thr Pro Gly Lys
                355                 360                 365

<210> SEQ ID NO 19
<211> LENGTH: 1104
<212> TYPE: DNA
<213> ORGANISM: Artificial sequence
<220> FEATURE:
<223> OTHER INFORMATION: Synthetic polynucleotide

<400> SEQUENCE: 19
cgtttaaacg gtaccgccgc caccatgggc tggtcctgca tcatcctgtt tctggtggcc     60
accgccacag gcgtccactc tggagacgcc aatccttcac tcgaattccg tctcgctaaa    120
acaacagccc catcggtcta tccactggcc cctgtgtgtg gagatacaac tggctcctcg    180
gtgactctag gatgcctggt caagggttat ttccctgagc cagtgacctt gacctggaac    240
```

-continued

```
tctggatccc tgtccagtgg tgtgcacacc ttcccagctg tcctgcagtc tgacctctac       300
accctcagca gctcagtgac tgtaacctcg agcacctggc ccagccagtc catcacctgc       360
aatgtggccc acccggcaag cagcaccaag gtggacaaga aaattgagcc cagagggccc       420
acaatcaagc cctgtcctcc atgcaaatgc ccagcaccta acctcttggg tggaccagac       480
gtcttcatct tccctccaaa gatcaaggat gtactcatga tctccctgag ccccatagtc       540
acatgtgtgg tggtggatgt gagcgaggat gacccagatg tccagatcag ctggtttgtg       600
aacaacgtgg aagtacacac agctcagaca caaacccata gagaggatta caacagtact       660
ctccgggtgg tcagtgccct ccccatccag caccaggact ggatgagtgg caaggagttc       720
aaatgcaagg tcaacaacaa agacctccca gcgcccgaag agaaccatct caaaaccc        780 aaagggtcag taagagctcc acaggtatat gtcttgcctc caccagaaga agagatgact       840
aagaaacagg tcactctgtg gtgcatggtc acagacttca tgcctgaaga catttacgtg       900
gagtggacca acaacgggaa aacagagcta aactacaaga acactgaacc agtcctggac       960
tctgatggtt cttacttcat gtacagcaag ctgagagtgg aaaagaagaa ctgggtggaa      1020
agaaatagct actcctgttc agtggtccac gagggtctgc acaatcacca cacgactaag      1080
agcttctccc ggactccggg taaa                                              1104
```

<210> SEQ ID NO 20
<211> LENGTH: 368
<212> TYPE: PRT
<213> ORGANISM: Artificial sequence
<220> FEATURE:
<223> OTHER INFORMATION: Synthetic polypeptide

<400> SEQUENCE: 20

```
Arg Leu Asn Gly Thr Ala Ala Thr Met Gly Trp Ser Cys Ile Ile Leu
1               5                   10                  15

Phe Leu Val Ala Thr Ala Thr Gly Val His Ser Gly Asp Ala Asn Pro
            20                  25                  30

Ser Leu Glu Phe Arg Leu Ala Lys Thr Thr Ala Pro Ser Val Tyr Pro
        35                  40                  45

Leu Ala Pro Val Cys Gly Asp Thr Thr Gly Ser Ser Val Thr Leu Gly
    50                  55                  60

Cys Leu Val Lys Gly Tyr Phe Pro Glu Pro Val Thr Leu Thr Trp Asn
65                  70                  75                  80

Ser Gly Ser Leu Ser Ser Gly Val His Thr Phe Pro Ala Val Leu Gln
                85                  90                  95

Ser Asp Leu Tyr Thr Leu Ser Ser Ser Val Thr Val Thr Ser Ser Thr
            100                 105                 110

Trp Pro Ser Gln Ser Ile Thr Cys Asn Val Ala His Pro Ala Ser Ser
        115                 120                 125

Thr Lys Val Asp Lys Lys Ile Glu Pro Arg Gly Pro Thr Ile Lys Pro
    130                 135                 140

Cys Pro Pro Cys Lys Cys Pro Ala Pro Asn Leu Leu Gly Gly Pro Asp
145                 150                 155                 160

Val Phe Ile Phe Pro Pro Lys Ile Lys Asp Val Leu Met Ile Ser Leu
                165                 170                 175

Ser Pro Ile Val Thr Cys Val Val Val Asp Val Ser Glu Asp Asp Pro
            180                 185                 190

Asp Val Gln Ile Ser Trp Phe Val Asn Asn Val Glu Val His Thr Ala
        195                 200                 205
```

```
Gln Thr Gln Thr His Arg Glu Asp Tyr Asn Ser Thr Leu Arg Val Val
    210                 215                 220

Ser Ala Leu Pro Ile Gln His Gln Asp Trp Met Ser Gly Lys Glu Phe
225                 230                 235                 240

Lys Cys Lys Val Asn Asn Lys Asp Leu Pro Ala Pro Glu Glu Arg Thr
                245                 250                 255

Ile Ser Lys Pro Lys Gly Ser Val Arg Ala Pro Gln Val Tyr Val Leu
            260                 265                 270

Pro Pro Pro Glu Glu Met Thr Lys Lys Gln Val Thr Leu Trp Cys
        275                 280                 285

Met Val Thr Asp Phe Met Pro Glu Asp Ile Tyr Val Glu Trp Thr Asn
    290                 295                 300

Asn Gly Lys Thr Glu Leu Asn Tyr Lys Asn Thr Glu Pro Val Leu Asp
305                 310                 315                 320

Ser Asp Gly Ser Tyr Phe Met Tyr Ser Lys Leu Arg Val Glu Lys Lys
                325                 330                 335

Asn Trp Val Glu Arg Asn Ser Tyr Ser Cys Ser Val Val His Glu Gly
            340                 345                 350

Leu His Asn His His Thr Thr Lys Ser Phe Ser Arg Thr Pro Gly Lys
        355                 360                 365

<210> SEQ ID NO 21
<211> LENGTH: 813
<212> TYPE: DNA
<213> ORGANISM: Artificial sequence
<220> FEATURE:
<223> OTHER INFORMATION: Synthetic polynucleotide

<400> SEQUENCE: 21
cgtttaaacg gtaccgccgc caccatgggc tggtcctgca tcatcctgtt tctggtggcc      60
accgccacag gcgtccactc tggagacgcc aatccttcac tcgaattccg tctcgagccc     120
agagggccca caatcaagcc ctgtcctcca tgcaaatgcc cagcacctaa cctcttgggt     180
ggaccagacg tcttcatctt ccctccaaag atcaaggatg tactcatgat ctccctgagc     240
cccatagtca catgtgtggt ggtggatgtg agcgaggatg acccagatgt ccagatcagc     300
tggtttgtga acaacgtgga agtacacaca gctcagacac aaacccatag agaggattac     360
aacagtactc tccgggtggt cagtgccctc ccatccagc accaggactg gatgagtggc     420
aaggagttca atgcaaggt caacaacaaa gacctcccag cgcccgaaga gagaaccatc     480
tcaaaaccca aagggtcagt aagagctcca caggtatatg tcttgcctcc accagaagaa     540
gagatgacta agaaacaggt cactctgtcc tgcgctgtca cagacttcat gcctgaagac     600
atttacgtgg agtggaccaa caacgggaaa acagagctaa actacaagaa cactgaacca     660
gtcctggact ctgatggttc ttacttcatg gtgagcaagc tgagagtgga aaagaagaac     720
tgggtggaaa gaatagcta ctcctgttca gtggtccacg agggtctgca caatcaccac     780
acgactaaga gcttctcccg gactccgggt aaa                                  813

<210> SEQ ID NO 22
<211> LENGTH: 271
<212> TYPE: PRT
<213> ORGANISM: Artificial sequence
<220> FEATURE:
<223> OTHER INFORMATION: Synthetic polypeptide

<400> SEQUENCE: 22

Arg Leu Asn Gly Thr Ala Ala Thr Met Gly Trp Ser Cys Ile Ile Leu
```

```
                1               5                    10                       15
            Phe Leu Val Ala Thr Ala Thr Gly Val His Ser Gly Asp Ala Asn Pro
                            20                   25                      30

Ser Leu Glu Phe Arg Leu Glu Pro Arg Gly Pro Thr Ile Lys Pro Cys
                            35                   40                      45

Pro Pro Cys Lys Cys Pro Ala Pro Asn Leu Leu Gly Gly Pro Asp Val
                            50                   55                      60

Phe Ile Phe Pro Pro Lys Ile Lys Asp Val Leu Met Ile Ser Leu Ser
            65                  70                   75                      80

Pro Ile Val Thr Cys Val Val Asp Val Ser Glu Asp Asp Pro Asp
                            85                   90                      95

Val Gln Ile Ser Trp Phe Val Asn Asn Val Glu Val His Thr Ala Gln
                            100                  105                     110

Thr Gln Thr His Arg Glu Asp Tyr Asn Ser Thr Leu Arg Val Val Ser
                            115                  120                     125

Ala Leu Pro Ile Gln His Gln Asp Trp Met Ser Gly Lys Glu Phe Lys
                            130                  135                     140

Cys Lys Val Asn Asn Lys Asp Leu Pro Ala Pro Glu Glu Arg Thr Ile
            145                 150                  155                     160

Ser Lys Pro Lys Gly Ser Val Arg Ala Pro Gln Val Tyr Val Leu Pro
                            165                  170                     175

Pro Pro Glu Glu Glu Met Thr Lys Lys Gln Val Thr Leu Ser Cys Ala
                            180                  185                     190

Val Thr Asp Phe Met Pro Glu Asp Ile Tyr Val Glu Trp Thr Asn Asn
                            195                  200                     205

Gly Lys Thr Glu Leu Asn Tyr Lys Asn Thr Glu Pro Val Leu Asp Ser
                            210                  215                     220

Asp Gly Ser Tyr Phe Met Val Ser Lys Leu Arg Val Glu Lys Lys Asn
            225                 230                  235                     240

Trp Val Glu Arg Asn Ser Tyr Ser Cys Ser Val Val His Glu Gly Leu
                            245                  250                     255

His Asn His His Thr Thr Lys Ser Phe Ser Arg Thr Pro Gly Lys
                            260                  265                     270

<210> SEQ ID NO 23
<211> LENGTH: 813
<212> TYPE: DNA
<213> ORGANISM: Artificial sequence
<220> FEATURE:
<223> OTHER INFORMATION: Synthetic polynucleotide

<400> SEQUENCE: 23
cgtttaaacg gtaccgccgc caccatgggc tggtcctgca tcatcctgtt tctggtggcc      60
accgccacag gcgtccactc tggagacgcc aatccttcac tcgaattccg tctcgagccc     120
agagggccca caatcaagcc ctgtcctcca tgcaaatgcc cagcacctaa cctcttgggt     180
ggaccagacg tcttcatctt ccctccaaag atcaaggatg tactcatgat ctccctgagc     240
cccatagtca catgtgtggt ggtggatgtg agcgaggatg acccagatgt ccagatcagc     300
tggtttgtga acaacgtgga agtacacaca gctcagacac aaacccatag agaggattac     360
aacagtactc tccgggtggt cagtgccctc cccatccagc accaggactg gatgagtggc     420
aaggagttca atgcaaggt caacaacaaa gacctcccag cgcccgaaga gagaaccatc      480
tcaaaaccca agggtcagt aagagctcca caggtatatg tcttgcctcc accagaagaa     540
gagatgacta agaaacaggt cactctgtgt ggtgcatggtca cagacttcat gcctgaagac     600
```

```
atttacgtgg agtggaccaa caacgggaaa acagagctaa actacaagaa cactgaacca    660
gtcctggact ctgatggttc ttacttcatg tacagcaagc tgagagtgga aaagaagaac    720
tgggtggaaa gaaatagcta ctcctgttca gtggtccacg agggtctgca caatcaccac    780
acgactaaga gcttctcccg gactccgggt aaa                                 813
```

```
<210> SEQ ID NO 24
<211> LENGTH: 271
<212> TYPE: PRT
<213> ORGANISM: Artificial sequence
<220> FEATURE:
<223> OTHER INFORMATION: Synthetic polypeptide

<400> SEQUENCE: 24
```

Arg Leu Asn Gly Thr Ala Ala Thr Met Gly Trp Ser Cys Ile Ile Leu
1               5                   10                  15

Phe Leu Val Ala Thr Ala Gly Val His Ser Gly Asp Ala Asn Pro
            20                  25                  30

Ser Leu Glu Phe Arg Leu Glu Pro Arg Gly Pro Thr Ile Lys Pro Cys
        35                  40                  45

Pro Pro Cys Lys Cys Pro Ala Pro Asn Leu Leu Gly Gly Pro Asp Val
    50                  55                  60

Phe Ile Phe Pro Pro Lys Ile Lys Asp Val Leu Met Ile Ser Leu Ser
65                  70                  75                  80

Pro Ile Val Thr Cys Val Val Asp Val Ser Glu Asp Asp Pro Asp
                85                  90                  95

Val Gln Ile Ser Trp Phe Val Asn Asn Val Glu Val His Thr Ala Gln
            100                 105                 110

Thr Gln Thr His Arg Glu Asp Tyr Asn Ser Thr Leu Arg Val Val Ser
        115                 120                 125

Ala Leu Pro Ile Gln His Gln Asp Trp Met Ser Gly Lys Glu Phe Lys
    130                 135                 140

Cys Lys Val Asn Asn Lys Asp Leu Pro Ala Pro Glu Glu Arg Thr Ile
145                 150                 155                 160

Ser Lys Pro Lys Gly Ser Val Arg Ala Pro Gln Val Tyr Val Leu Pro
                165                 170                 175

Pro Pro Glu Glu Glu Met Thr Lys Lys Gln Val Thr Leu Trp Cys Met
            180                 185                 190

Val Thr Asp Phe Met Pro Glu Asp Ile Tyr Val Glu Trp Thr Asn Asn
        195                 200                 205

Gly Lys Thr Glu Leu Asn Tyr Lys Asn Thr Glu Pro Val Leu Asp Ser
    210                 215                 220

Asp Gly Ser Tyr Phe Met Tyr Ser Lys Leu Arg Val Glu Lys Lys Asn
225                 230                 235                 240

Trp Val Glu Arg Asn Ser Tyr Ser Cys Ser Val Val His Glu Gly Leu
                245                 250                 255

His Asn His His Thr Thr Lys Ser Phe Ser Arg Thr Pro Gly Lys
            260                 265                 270

```
<210> SEQ ID NO 25
<211> LENGTH: 991
<212> TYPE: DNA
<213> ORGANISM: Artificial sequence
<220> FEATURE:
<223> OTHER INFORMATION: Synthetic polynucleotide

<400> SEQUENCE: 25
```

```
agtttaaacg gtaccgccgc caccatgggc tggtcctgca tcatcctgtt tctggtggcc    60
accgccacag gcgtccactc tggagacgcc tccttaacac tcgaattccg tctcgctaaa   120
acaacagccc catcggtcta tccactggcc cctgtgtgtg agatacaac tggctcctcg    180
gtgactctag gatgcctggt caagggttat ttccctgagc cagtgacctt gacctggaac   240
tctggatccc tgtccagtgg tgtgcacacc ttcccagctg tcctgcagtc tgacctctac   300
accctcagca gctcagtgac tgtaacctcg agcacctggc ccagccagtc catcacctgc   360
aatgtggccc acccggcaag cagcaccaag gtggacaaga aaattgagcc cagagggccc   420
acaatcaagc cctgtcctcc atgcaaatgc ccagcaccta acctcttggg tggaccatcc   480
gtcttcatct cccctccaaa gatcaaggat gtactcatga tctccctgag ccccatagtc   540
acatgtgtgg tggtggatgt gagcgaggat gacccagatg tccagatcag ctggtttgtg   600
aacaacgtgg aagtacacac agctcagaca caaacccata gagaggatta caacagtact   660
ctccgggtgg tcagtgccct ccccatccag caccaggact ggatgagtgg caaggagttc   720
aaatgcaagg tcaacaacaa agacctccca gcgcccatcg agaaccat ctcaaaaccc     780
aaagggtcag taagagctcc acaggtatat gtcttgcctc caccagaaga agagatgact   840
aagaaacagg tcactctgac ctgcatggtc acagacttca tgcctgaaga catttacgtg   900
gagtggacca acaacgggaa aacagagcta aactacaaga cactgaacc agtcctggac   960
tctgatggtt cttacttcat gtacagcaag c                                   991

<210> SEQ ID NO 26
<211> LENGTH: 330
<212> TYPE: PRT
<213> ORGANISM: Artificial sequence
<220> FEATURE:
<223> OTHER INFORMATION: Synthetic polypeptide

<400> SEQUENCE: 26

Ser Leu Asn Gly Thr Ala Ala Thr Met Gly Trp Ser Cys Ile Ile Leu
1               5                   10                  15

Phe Leu Val Ala Thr Ala Thr Gly Val His Ser Gly Asp Ala Ser Leu
                20                  25                  30

Thr Leu Glu Phe Arg Leu Ala Lys Thr Thr Ala Pro Ser Val Tyr Pro
            35                  40                  45

Leu Ala Pro Val Cys Gly Asp Thr Thr Gly Ser Ser Val Thr Leu Gly
        50                  55                  60

Cys Leu Val Lys Gly Tyr Phe Pro Glu Pro Val Thr Leu Thr Trp Asn
65                  70                  75                  80

Ser Gly Ser Leu Ser Ser Gly Val His Thr Phe Pro Ala Val Leu Gln
                85                  90                  95

Ser Asp Leu Tyr Thr Leu Ser Ser Ser Val Thr Val Thr Ser Ser Thr
                100                 105                 110

Trp Pro Ser Gln Ser Ile Thr Cys Asn Val Ala His Pro Ala Ser Ser
            115                 120                 125

Thr Lys Val Asp Lys Lys Ile Glu Pro Arg Gly Pro Thr Ile Lys Pro
        130                 135                 140

Cys Pro Pro Cys Lys Cys Pro Ala Pro Asn Leu Leu Gly Gly Pro Ser
145                 150                 155                 160

Val Phe Ile Phe Pro Pro Lys Ile Lys Asp Val Leu Met Ile Ser Leu
                165                 170                 175

Ser Pro Ile Val Thr Cys Val Val Val Asp Val Ser Glu Asp Asp Pro
```

```
                180                 185                 190
Asp Val Gln Ile Ser Trp Phe Val Asn Asn Val Glu Val His Thr Ala
            195                 200                 205

Gln Thr Gln Thr His Arg Glu Asp Tyr Asn Ser Thr Leu Arg Val Val
210                 215                 220

Ser Ala Leu Pro Ile Gln His Gln Asp Trp Met Ser Gly Lys Glu Phe
225                 230                 235                 240

Lys Cys Lys Val Asn Asn Lys Asp Leu Pro Ala Pro Ile Glu Arg Thr
                245                 250                 255

Ile Ser Lys Pro Lys Gly Ser Val Arg Ala Pro Gln Val Tyr Val Leu
            260                 265                 270

Pro Pro Pro Glu Glu Glu Met Thr Lys Lys Gln Val Thr Leu Thr Cys
        275                 280                 285

Met Val Thr Asp Phe Met Pro Glu Asp Ile Tyr Val Glu Trp Thr Asn
    290                 295                 300

Asn Gly Lys Thr Glu Leu Asn Tyr Lys Asn Thr Glu Pro Val Leu Asp
305                 310                 315                 320

Ser Asp Gly Ser Tyr Phe Met Tyr Ser Lys
                325                 330

<210> SEQ ID NO 27
<211> LENGTH: 330
<212> TYPE: PRT
<213> ORGANISM: Artificial sequence
<220> FEATURE:
<223> OTHER INFORMATION: Synthetic polypeptide

<400> SEQUENCE: 27

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Asp Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Gln Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Glu Glu Arg Thr Ile Ser Lys Pro Lys Gly
```

```
            210                 215                 220
Ser Val Arg Ala Pro Gln Val Tyr Val Leu Pro Pro Glu Glu Glu
225                 230                 235                 240

Met Thr Lys Lys Gln Val Thr Leu Ser Cys Ala Val Thr Asp Phe Met
                245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
            275                 280                 285

Met Val Ser Lys Leu Arg Val Glu Lys Lys Asn Trp Val Glu Arg Asn
        290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 28
<211> LENGTH: 233
<212> TYPE: PRT
<213> ORGANISM: Artificial sequence
<220> FEATURE:
<223> OTHER INFORMATION: Synthetic polypeptide

<400> SEQUENCE: 28

Glu Pro Arg Gly Pro Thr Ile Lys Pro Cys Pro Pro Cys Lys Cys Pro
1               5                   10                  15

Ala Pro Asn Leu Leu Gly Gly Pro Asp Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Glu Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140

Thr Lys Lys Gln Val Thr Leu Trp Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230
```

-continued

```
<210> SEQ ID NO 29
<211> LENGTH: 242
<212> TYPE: PRT
<213> ORGANISM: Artificial sequence
<220> FEATURE:
<223> OTHER INFORMATION: Synthetic polypeptide

<400> SEQUENCE: 29

Gly Gly Gly Gly Ser Gly Gly Gly Ser Glu Pro Arg Gly Pro Thr
1               5                   10                  15

Ile Lys Pro Cys Pro Pro Cys Lys Cys Pro Ala Pro Asn Leu Leu Gly
            20                  25                  30

Gly Pro Ser Val Phe Ile Phe Pro Lys Ile Lys Asp Val Leu Met
            35                  40                  45

Ile Ser Leu Ser Pro Ile Val Thr Cys Val Val Asp Val Ser Glu
50                  55                  60

Asp Pro Asp Val Gln Ile Ser Trp Phe Val Asn Asn Val Glu Val
65                  70                  75                  80

His Thr Ala Gln Thr Gln Thr His Arg Glu Asp Tyr Ala Ser Thr Leu
                85                  90                  95

Arg Val Val Ser Ala Leu Pro Ile Gln His Gln Asp Trp Met Ser Gly
            100                 105                 110

Lys Glu Phe Lys Cys Lys Val Asn Asn Lys Asp Leu Pro Ala Pro Ile
        115                 120                 125

Glu Arg Thr Ile Ser Lys Pro Lys Gly Ser Val Arg Ala Pro Gln Val
    130                 135                 140

Tyr Val Leu Pro Pro Pro Glu Glu Glu Met Thr Lys Lys Gln Val Thr
145                 150                 155                 160

Leu Trp Cys Met Val Thr Asp Phe Met Pro Glu Asp Ile Tyr Val Glu
                165                 170                 175

Trp Thr Asn Asn Gly Lys Thr Glu Leu Asn Tyr Lys Asn Thr Glu Pro
            180                 185                 190

Val Leu Asp Ser Asp Gly Ser Tyr Phe Met Tyr Ser Lys Leu Arg Val
        195                 200                 205

Glu Lys Lys Asn Trp Val Glu Arg Asn Ser Tyr Ser Cys Ser Val Val
    210                 215                 220

His Glu Gly Leu His Asn His His Thr Thr Lys Ser Phe Ser Arg Thr
225                 230                 235                 240

Pro Gly

<210> SEQ ID NO 30
<211> LENGTH: 242
<212> TYPE: PRT
<213> ORGANISM: Artificial sequence
<220> FEATURE:
<223> OTHER INFORMATION: Synthetic polypeptide

<400> SEQUENCE: 30

Gly Gly Gly Gly Ser Gly Gly Gly Ser Glu Pro Arg Gly Pro Thr
1               5                   10                  15

Ile Lys Pro Cys Pro Pro Cys Lys Cys Pro Ala Pro Asn Leu Leu Gly
            20                  25                  30

Gly Pro Ser Val Phe Ile Phe Pro Lys Ile Lys Asp Val Leu Met
            35                  40                  45

Ile Ser Leu Ser Pro Ile Val Thr Cys Val Val Asp Val Ser Glu
50                  55                  60

Asp Asp Pro Asp Val Gln Ile Ser Trp Phe Val Asn Asn Val Glu Val
```

```
        65                  70                  75                  80
His Thr Ala Gln Thr Gln Thr His Arg Glu Asp Tyr Ala Ser Thr Leu
                85                  90                  95

Arg Val Val Ser Ala Leu Pro Ile Gln His Gln Asp Trp Met Ser Gly
                100                 105                 110

Lys Glu Phe Lys Cys Lys Val Asn Asn Lys Asp Leu Pro Ala Pro Ile
                115                 120                 125

Glu Arg Thr Ile Ser Lys Pro Lys Gly Ser Val Arg Ala Pro Gln Val
                130                 135                 140

Tyr Val Leu Pro Pro Glu Glu Met Thr Lys Lys Gln Val Thr
145                 150                 155                 160

Leu Trp Cys Met Val Thr Asp Phe Met Pro Glu Asp Ile Tyr Val Glu
                165                 170                 175

Trp Thr Asn Asn Gly Lys Thr Glu Leu Asn Tyr Lys Asn Thr Glu Pro
                180                 185                 190

Val Leu Asp Ser Asp Gly Ser Tyr Phe Met Tyr Ser Lys Leu Arg Val
                195                 200                 205

Glu Lys Lys Asn Trp Val Glu Arg Asn Ser Tyr Ser Cys Ser Val Val
                210                 215                 220

His Glu Gly Leu His Asn His His Thr Thr Lys Ser Phe Ser Arg Thr
225                 230                 235                 240

Pro Gly

<210> SEQ ID NO 31
<211> LENGTH: 330
<212> TYPE: PRT
<213> ORGANISM: Artificial sequence
<220> FEATURE:
<223> OTHER INFORMATION: Synthetic polypeptide

<400> SEQUENCE: 31

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
                35                  40                  45

Gly Val His Thr Phe Pro Ala Val Leu Gln Ser Asp Leu Tyr Thr Leu
                50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
                100                 105                 110

Pro Ala Pro Asn Leu Leu Gly Gly Pro Ser Val Phe Ile Phe Pro Pro
                115                 120                 125

Lys Ile Lys Asp Val Leu Met Ile Ser Leu Ser Pro Ile Val Thr Cys
                130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Ala Ser Thr Leu Arg Val Val Ser Ala Leu Pro Ile Gln
                180                 185                 190
```

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
        210                 215                 220

Ser Val Arg Ala Pro Gln Val Tyr Val Leu Pro Pro Pro Glu Glu Glu
225                 230                 235                 240

Met Thr Lys Lys Gln Val Thr Leu Ser Cys Ala Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Val Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 32
<211> LENGTH: 373
<212> TYPE: PRT
<213> ORGANISM: Artificial sequence
<220> FEATURE:
<223> OTHER INFORMATION: Synthetic polypeptide

<400> SEQUENCE: 32

Arg Leu Asn Gly Thr Ala Ala Thr Met Gly Trp Ser Cys Ile Ile Leu
1               5                   10                  15

Phe Leu Val Ala Thr Ala Thr Gly Val His Ser Gly Asp Ala Asn Pro
            20                  25                  30

Ser Leu Glu Phe Arg Leu Ala Lys Thr Thr Ala Pro Ser Val Tyr Pro
        35                  40                  45

Leu Ala Pro Val Cys Gly Asp Thr Thr Gly Ser Ser Val Thr Leu Gly
    50                  55                  60

Cys Leu Val Lys Gly Tyr Phe Pro Glu Pro Val Thr Leu Thr Trp Asn
65                  70                  75                  80

Ser Gly Ser Leu Ser Ser Gly Val His Thr Phe Pro Ala Val Leu Gln
                85                  90                  95

Ser Asp Leu Tyr Thr Leu Ser Ser Ser Val Thr Val Thr Ser Ser Thr
            100                 105                 110

Trp Pro Ser Gln Ser Ile Thr Cys Asn Val Ala His Pro Ala Ser Ser
        115                 120                 125

Thr Lys Val Asp Lys Lys Ile Glu Pro Arg Gly Pro Thr Ile Lys Pro
    130                 135                 140

Cys Pro Pro Cys Lys Cys Pro Ala Pro Asn Leu Leu Gly Gly Pro Asp
145                 150                 155                 160

Val Phe Ile Phe Pro Pro Lys Ile Lys Asp Val Leu Met Ile Ser Leu
                165                 170                 175

Ser Pro Ile Val Thr Cys Val Val Asp Val Ser Glu Asp Asp Pro
            180                 185                 190

Asp Val Gln Ile Ser Trp Phe Val Asn Asn Val Glu Val His Thr Ala
        195                 200                 205

Gln Thr Gln Thr His Arg Glu Asp Tyr Gln Ser Thr Leu Arg Val Val
    210                 215                 220

```
Ser Ala Leu Pro Ile Gln His Gln Asp Trp Met Ser Gly Lys Glu Phe
225                 230                 235                 240

Lys Cys Lys Val Asn Asn Lys Asp Leu Pro Ala Pro Glu Glu Arg Thr
                245                 250                 255

Ile Ser Lys Pro Lys Gly Ser Val Arg Ala Pro Gln Val Tyr Val Leu
            260                 265                 270

Pro Pro Pro Glu Glu Met Thr Lys Lys Gln Val Thr Leu Ser Cys
            275                 280                 285

Ala Val Thr Asp Phe Met Pro Glu Asp Ile Tyr Val Glu Trp Thr Asn
290                 295                 300

Asn Gly Lys Thr Glu Leu Asn Tyr Lys Asn Thr Glu Pro Val Leu Asp
305                 310                 315                 320

Ser Asp Gly Ser Tyr Phe Met Val Ser Lys Leu Arg Val Glu Lys Lys
                325                 330                 335

Asn Trp Val Glu Arg Asn Ser Tyr Ser Cys Ser Val Val His Glu Gly
                340                 345                 350

Leu His Asn His His Thr Thr Lys Ser Phe Ser Arg Thr Pro Gly Lys
                355                 360                 365

Ser Arg Ala Ala Ala
    370
```

<210> SEQ ID NO 33
<211> LENGTH: 373
<212> TYPE: PRT
<213> ORGANISM: Artificial sequence
<220> FEATURE:
<223> OTHER INFORMATION: Synthetic polypeptide

<400> SEQUENCE: 33

```
Arg Leu Asn Gly Thr Ala Ala Thr Met Gly Trp Ser Cys Ile Ile Leu
1               5                   10                  15

Phe Leu Val Ala Thr Ala Thr Gly Val His Ser Gly Asp Ala Asn Pro
                20                  25                  30

Ser Leu Glu Phe Arg Leu Ala Lys Thr Thr Ala Pro Ser Val Tyr Pro
            35                  40                  45

Leu Ala Pro Val Cys Gly Asp Thr Thr Gly Ser Ser Val Thr Leu Gly
50                  55                  60

Cys Leu Val Lys Gly Tyr Phe Pro Glu Pro Val Thr Leu Thr Trp Asn
65                  70                  75                  80

Ser Gly Ser Leu Ser Ser Gly Val His Thr Phe Pro Ala Val Leu Gln
                85                  90                  95

Ser Asp Leu Tyr Thr Leu Ser Ser Ser Val Thr Val Thr Ser Ser Thr
            100                 105                 110

Trp Pro Ser Gln Ser Ile Thr Cys Asn Val Ala His Pro Ala Ser Ser
        115                 120                 125

Thr Lys Val Asp Lys Lys Ile Glu Pro Arg Gly Pro Thr Ile Lys Pro
    130                 135                 140

Cys Pro Pro Cys Lys Cys Pro Ala Pro Asn Leu Leu Gly Gly Pro Asp
145                 150                 155                 160

Val Phe Ile Phe Pro Pro Lys Ile Lys Asp Val Leu Met Ile Ser Leu
                165                 170                 175

Ser Pro Ile Val Thr Cys Val Val Val Asp Val Ser Glu Asp Asp Pro
            180                 185                 190

Asp Val Gln Ile Ser Trp Phe Val Asn Asn Val Glu Val His Thr Ala
        195                 200                 205
```

-continued

Gln Thr Gln Thr His Arg Glu Asp Tyr Asn Ser Thr Leu Arg Val Val
    210                 215                 220

Ser Ala Leu Pro Ile Gln His Gln Asp Trp Met Ser Gly Lys Glu Phe
225                 230                 235                 240

Lys Cys Lys Val Asn Asn Lys Asp Leu Pro Ala Pro Glu Glu Arg Thr
                245                 250                 255

Ile Ser Lys Pro Lys Gly Ser Val Arg Ala Pro Gln Val Tyr Val Leu
            260                 265                 270

Pro Pro Pro Glu Glu Glu Met Thr Lys Lys Gln Val Thr Leu Trp Cys
        275                 280                 285

Met Val Thr Asp Phe Met Pro Glu Asp Ile Tyr Val Glu Trp Thr Asn
290                 295                 300

Asn Gly Lys Thr Glu Leu Asn Tyr Lys Asn Thr Glu Pro Val Leu Asp
305                 310                 315                 320

Ser Asp Gly Ser Tyr Phe Met Tyr Ser Lys Leu Arg Val Glu Lys Lys
                325                 330                 335

Asn Trp Val Glu Arg Asn Ser Tyr Ser Cys Ser Val Val His Glu Gly
            340                 345                 350

Leu His Asn His His Thr Thr Lys Ser Phe Ser Arg Thr Pro Gly Lys
        355                 360                 365

Ser Arg Ala Ala Ala
    370

<210> SEQ ID NO 34
<211> LENGTH: 276
<212> TYPE: PRT
<213> ORGANISM: Artificial sequence
<220> FEATURE:
<223> OTHER INFORMATION: Synthetic polypeptide

<400> SEQUENCE: 34

Arg Leu Asn Gly Thr Ala Ala Thr Met Gly Trp Ser Cys Ile Ile Leu
1               5                   10                  15

Phe Leu Val Ala Thr Ala Thr Gly Val His Ser Gly Asp Ala Asn Pro
                20                  25                  30

Ser Leu Glu Phe Arg Leu Glu Pro Arg Gly Pro Thr Ile Lys Pro Cys
            35                  40                  45

Pro Pro Cys Lys Cys Pro Ala Pro Asn Leu Leu Gly Gly Pro Asp Val
        50                  55                  60

Phe Ile Phe Pro Pro Lys Ile Lys Asp Val Leu Met Ile Ser Leu Ser
65                  70                  75                  80

Pro Ile Val Thr Cys Val Val Asp Val Ser Glu Asp Asp Pro Asp
                85                  90                  95

Val Gln Ile Ser Trp Phe Val Asn Asn Val Glu Val His Thr Ala Gln
                100                 105                 110

Thr Gln Thr His Arg Glu Asp Tyr Asn Ser Thr Leu Arg Val Val Ser
            115                 120                 125

Ala Leu Pro Ile Gln His Gln Asp Trp Met Ser Gly Lys Glu Phe Lys
        130                 135                 140

Cys Lys Val Asn Asn Lys Asp Leu Pro Ala Pro Glu Glu Arg Thr Ile
145                 150                 155                 160

Ser Lys Pro Lys Gly Ser Val Arg Ala Pro Gln Val Tyr Val Leu Pro
                165                 170                 175

Pro Pro Glu Glu Glu Met Thr Lys Lys Gln Val Thr Leu Ser Cys Ala
            180                 185                 190

```
Val Thr Asp Phe Met Pro Glu Asp Ile Tyr Val Glu Trp Thr Asn Asn
            195                 200                 205

Gly Lys Thr Glu Leu Asn Tyr Lys Asn Thr Glu Pro Val Leu Asp Ser
        210                 215                 220

Asp Gly Ser Tyr Phe Met Val Ser Lys Leu Arg Val Glu Lys Lys Asn
225                 230                 235                 240

Trp Val Glu Arg Asn Ser Tyr Ser Cys Ser Val Val His Glu Gly Leu
                245                 250                 255

His Asn His His Thr Thr Lys Ser Phe Ser Arg Thr Pro Gly Lys Ser
            260                 265                 270

Arg Ala Ala Ala
        275

<210> SEQ ID NO 35
<211> LENGTH: 276
<212> TYPE: PRT
<213> ORGANISM: Artificial sequence
<220> FEATURE:
<223> OTHER INFORMATION: Synthetic polypeptide

<400> SEQUENCE: 35

Arg Leu Asn Gly Thr Ala Ala Thr Met Gly Trp Ser Cys Ile Ile Leu
1               5                   10                  15

Phe Leu Val Ala Thr Ala Thr Gly Val His Ser Gly Asp Ala Asn Pro
            20                  25                  30

Ser Leu Glu Phe Arg Leu Glu Pro Arg Gly Pro Thr Ile Lys Pro Cys
        35                  40                  45

Pro Pro Cys Lys Cys Pro Ala Pro Asn Leu Leu Gly Gly Pro Asp Val
50                  55                  60

Phe Ile Phe Pro Pro Lys Ile Lys Asp Val Leu Met Ile Ser Leu Ser
65                  70                  75                  80

Pro Ile Val Thr Cys Val Val Asp Val Ser Glu Asp Asp Pro Asp
                85                  90                  95

Val Gln Ile Ser Trp Phe Val Asn Asn Val Glu Val His Thr Ala Gln
            100                 105                 110

Thr Gln Thr His Arg Glu Asp Tyr Asn Ser Thr Leu Arg Val Val Ser
        115                 120                 125

Ala Leu Pro Ile Gln His Gln Asp Trp Met Ser Gly Lys Glu Phe Lys
130                 135                 140

Cys Lys Val Asn Asn Lys Asp Leu Pro Ala Pro Glu Glu Arg Thr Ile
145                 150                 155                 160

Ser Lys Pro Lys Gly Ser Val Arg Ala Pro Gln Val Tyr Val Leu Pro
                165                 170                 175

Pro Pro Glu Glu Glu Met Thr Lys Lys Gln Val Thr Leu Trp Cys Met
            180                 185                 190

Val Thr Asp Phe Met Pro Glu Asp Ile Tyr Val Glu Trp Thr Asn Asn
        195                 200                 205

Gly Lys Thr Glu Leu Asn Tyr Lys Asn Thr Glu Pro Val Leu Asp Ser
    210                 215                 220

Asp Gly Ser Tyr Phe Met Tyr Ser Lys Leu Arg Val Glu Lys Lys Asn
225                 230                 235                 240

Trp Val Glu Arg Asn Ser Tyr Ser Cys Ser Val Val His Glu Gly Leu
                245                 250                 255

His Asn His His Thr Thr Lys Ser Phe Ser Arg Thr Pro Gly Lys Ser
            260                 265                 270
```

Arg Ala Ala Ala
        275

<210> SEQ ID NO 36
<211> LENGTH: 330
<212> TYPE: PRT
<213> ORGANISM: Artificial sequence
<220> FEATURE:
<223> OTHER INFORMATION: Synthetic polypeptide

<400> SEQUENCE: 36

Ser Leu Asn Gly Thr Ala Ala Thr Met Gly Trp Ser Cys Ile Ile Leu
1               5                   10                  15

Phe Leu Val Ala Thr Ala Thr Gly Val His Ser Gly Asp Ala Ser Leu
            20                  25                  30

Thr Leu Glu Phe Arg Leu Ala Lys Thr Thr Ala Pro Ser Val Tyr Pro
        35                  40                  45

Leu Ala Pro Val Cys Gly Asp Thr Thr Gly Ser Ser Val Thr Leu Gly
    50                  55                  60

Cys Leu Val Lys Gly Tyr Phe Pro Glu Pro Val Thr Leu Thr Trp Asn
65                  70                  75                  80

Ser Gly Ser Leu Ser Ser Gly Val His Thr Phe Pro Ala Val Leu Gln
                85                  90                  95

Ser Asp Leu Tyr Thr Leu Ser Ser Val Thr Val Thr Ser Ser Thr
            100                 105                 110

Trp Pro Ser Gln Ser Ile Thr Cys Asn Val Ala His Pro Ala Ser Ser
        115                 120                 125

Thr Lys Val Asp Lys Lys Ile Glu Pro Arg Gly Pro Thr Ile Lys Pro
130                 135                 140

Cys Pro Pro Cys Lys Cys Pro Ala Pro Asn Leu Leu Gly Gly Pro Ser
145                 150                 155                 160

Val Phe Ile Phe Pro Pro Lys Ile Lys Asp Val Leu Met Ile Ser Leu
                165                 170                 175

Ser Pro Ile Val Thr Cys Val Val Asp Val Ser Glu Asp Asp Pro
            180                 185                 190

Asp Val Gln Ile Ser Trp Phe Val Asn Asn Val Glu Val His Thr Ala
        195                 200                 205

Gln Thr Gln Thr His Arg Glu Asp Tyr Asn Ser Thr Leu Arg Val Val
    210                 215                 220

Ser Ala Leu Pro Ile Gln His Gln Asp Trp Met Ser Gly Lys Glu Phe
225                 230                 235                 240

Lys Cys Lys Val Asn Asn Lys Asp Leu Pro Ala Pro Ile Glu Arg Thr
                245                 250                 255

Ile Ser Lys Pro Lys Gly Ser Val Arg Ala Pro Gln Val Tyr Val Leu
            260                 265                 270

Pro Pro Pro Glu Glu Glu Met Thr Lys Lys Gln Val Thr Leu Thr Cys
        275                 280                 285

Met Val Thr Asp Phe Met Pro Glu Asp Ile Tyr Val Glu Trp Thr Asn
    290                 295                 300

Asn Gly Lys Thr Glu Leu Asn Tyr Lys Asn Thr Glu Pro Val Leu Asp
305                 310                 315                 320

Ser Asp Gly Ser Tyr Phe Met Tyr Ser Lys
                325                 330

BISPECIFIC ANTIGEN BINDING CONSTRUCT

RELATED APPLICATIONS

This application claims benefit of United States Provisional Patent Application No. 62/609,523, filed Dec. 22, 2017, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jan. 6, 2022, is named 607772_AGX5-031_ST25v2.txt and is 57,339 bytes in size.

FIELD OF THE INVENTION

The present invention relates to multispecific, e.g., bispecific, antigen binding constructs, comprising a conventional antibody and a VHH antibody for improved binding to protein complexes. The antigen binding constructs are capable of targeting at least two distinct antigens within the protein complex. The present invention further relates to multispecific antigen binding constructs, comprising a conventional antibody and a VHH antibody, for improved purification via, e.g., size exclusion chromatography (SEC).

BACKGROUND OF THE INVENTION

Naturally occurring antibodies, including bivalent antibodies, exhibit immunoreactivity to a specific epitope on a particular target antigen. Multispecific antibodies, as the name indicates, are antibodies engineered to recognize and bind more than one epitope, potentially on different target antigens of interest.

Naturally occurring conventional antibodies typically include combinations of heavy and light immunoglobulin chains, wherein the antigen binding properties of the molecule are determined by the variable regions or domains of the heavy and light chains, i.e., the VH and VL domains, respectively. More specifically, the antigen binding sites of conventional antibodies typically include residues contributed by three complementarity determining regions (CDRs) within each of the VH and VL domains.

Multispecific antibodies typically differ from naturally occurring antibodies in that they incorporate more than one VH-VL domain pairing such that they can recognize and bind to more than one epitope. Commercially these antibodies are extremely important for their ability to bind more than one target antigen. However, significant difficulties exist in the manufacture and isolation of multispecific antibodies as a result of mispairings between the different heavy chains and light chains incorporated into the same antibody molecule. These mispairings can lead to the inadvertent production of monospecific antibodies or antibodies having non-functional or non-productive antigen binding sites, thereby reducing the yield of the multispecific antibody of interest.

FIG. 1 illustrates the difficulties that can arise in the production of a bispecific antibody exhibiting immunoreactivity for two distinct epitopes. The bispecific antibody as shown (A) includes two distinct heavy chains and two distinct light chains. However, only the correct pairing of these four immunoglobulin chains gives rise to an antibody having the desired binding profile, i.e., specificity for both target antigens. There are in fact nine other potential combinations that can form from a mixture of the four heavy and light chains shown, which result in bivalent monospecific antibodies (E and H), monovalent monospecific antibodies (B, C, G and J) and non-binding antibodies (D, F and I). This problem becomes worse the more complex the multispecific antibody molecule, i.e., the more epitopes or antigens the antibody is intended to bind.

Various attempts have been made to improve multispecific antibody production by addressing the problem of incorrect chain pairing. Several approaches have focused on engineering antibodies so as to promote the correct pairing between VH-VL domains. For instance, US Patent Application No. 2010/0254989 A1 describes the construction of bispecific cMet-ErbB1 antibodies, where the VH and VL of the individual antibodies are fused genetically via a GlySer linker. An alternative approach uses rat-mouse quadromas for generating bispecific antibodies, where the mouse and the rat antibody predominantly forms the original VH-VL pairings and the bispecific antibody consists of the rat and the mouse Fc (Lindhofer et al., J Immunol. (1995) 155: 1246-1252).

For bispecific antibodies including an Fc domain, researchers have also focused on introducing mutations into the constant region of the heavy chains to promote the correct heterodimerization of the Fc portion. Several such techniques are reviewed in Klein et al. (mAbs (2012) 4:6, 1-11), the contents of which are incorporated herein by reference in their entirety. These techniques include the "knobs-into-holes" (KiH) approach which involves the introduction of a bulky residue into one of the CH3 domains of one of the antibody heavy chains. This bulky residue fits into a complementary "hole" in the other CH3 domain of the paired heavy chain so as to promote correct pairing of heavy chains.

Researchers have also attempted to resolve the problem of achieving correct association of heavy chain and light chain pairs. One approach uses the CrossMab principle (as reviewed in Klein et al.), which involves domain swapping between heavy and light chains so as to promote the formation of the correct pairings. Others have sought to engineer the interfaces between the paired VH-VL domains or paired CH1-CL domains of the heavy and light chains so as to increase the affinity between the heavy chain and its cognate light chain (Lewis et al., Nature Biotechnology (2014) 32: 191-198). Techniques such as those described above that require extensive antibody engineering have met with some success; however, the production of antibodies harbouring specific mutations can be labour intensive and can result in antibodies which are highly immunogenic in humans and/or suffer from a loss of effector function.

An alternative approach to the production of multispecific antibody preparations having the correct antigen specificity has been the development of methods that enrich for antibodies having the correct heavy chain-light chain pairings. For example, Spiess et al. (Nature Biotechnology (2013) 31: 753-758) describe a method for the production of a MET-EGFR bispecific antibody from a co-culture of bacteria expressing two distinct half-antibodies.

Methods have also been described wherein the constant region of at least one of the heavy chains of a bispecific antibody is mutated so as to alter its binding affinity for an affinity agent, for example Protein A. This allows correctly paired heavy chain heterodimers to be isolated based on a purification technique that exploits the differential binding of the two heavy chains to an affinity agent (see US Patent Application Publication No. 2010/0331527 and WO 2013/136186). The limitation with methods that select for correct heavy chain heterodimerization based on differential binding is that they do not select for antibodies having the correct heavy chain-light chain pairings such that these techniques are typically applied to multispecific antibodies having a shared or common light chain.

International patent application no. PCT/EP2012/071866 (WO 2013/064701) addresses the problem of incorrect chain pairing using a method for multispecific antibody isolation based on the use of anti-idiotypic binding agents, in particular anti-idiotypic antibodies. The anti-idiotype binding agents are employed in a two-step selection method in which a first agent is used to capture antibodies having a VH-VL domain pairing specific for a first antigen and a second agent is subsequently used to capture antibodies also having a second VH-VL domain pairing specific for a second antigen.

The drawback with this method is that the anti-idiotypic binding agents used to isolate the antibody must be specific for each multispecific antibody produced, depending on its antigen binding profile. Therefore, although the principle of the method described in PCT/EP2012/071866 is generally applicable to the isolation of any multispecific antibody, the reagents, i.e., the anti-idiotypic binding agents, must be generated in accordance with the specific VH-VL domain pairings of the multispecific antibody to be isolated.

SUMMARY OF THE INVENTION

The present invention improves upon the state of the art by providing multispecific antigen binding constructs having at least one conventional Fab binding region and one single domain antibody (VHH) binding region. This format, in combination with heterodimerization methods, forces the generation of one bispecific antibody configuration. The heterodimerization method employed forces the binding of the heavy chain region of the Fab and the full, heavy-chain-only VHH. Because the VHH chain does not associate with light chains, the light chain region of the Fab portion will only associate with its corresponding heavy chain.

The present invention further improves upon the state of the art by providing desired multispecific antigen binding constructs, e.g., bispecific antibodies, that may be purified from undesired antibodies based on size. The desired multispecific antigen binding constructs will have a size of about 112 kDa, while undesired antibodies will have sizes of about 150 kDa and/or 75 kDa.

In a first aspect, the present invention provides a bispecific antigen binding construct comprising:
(a) a single domain antibody (VHH) binding region which binds a first target antigen, wherein said single domain antibody binding region is operatively linked to a first IgG Fc domain polypeptide; and
(b) a Fab portion of a conventional IgG antibody which binds a second target antigen, wherein said Fab portion is operatively linked to a second IgG Fc domain polypeptide; wherein the first and second IgG Fc domain polypeptides dimerize to form the bispecific antigen binding construct.

In an embodiment, Fc domain dimerization occurs by knobs-into-holes interactions, Fab arm exchange (FAE), electrostatic steering interactions, or hydrophobic interactions.

In an embodiment, the first IgG Fc domain polypeptide contains a knob substitution, and the second IgG Fc domain polypeptide contains a hole substitution.

In an embodiment, the knob substitution is selected from the group consisting of arginine (R), phenylalanine (F), tyrosine (Y), tryptophan (W), and any combination thereof.

In an embodiment, the hole substitution is selected from the group consisting of alanine (A), asparagine (N), aspartic acid (D), glycine (G), serine (S), threonine (T), valine (V), and any combination thereof.

In an embodiment, the bispecific antigen binding construct has a molecular weight in the range of from about 100 kDa to about 120 kDa.

In an embodiment, the desired bispecific antigen binding construct is about 112 kDa.

In another aspect, the present invention provides a method of purifying a bispecific antigen binding construct, the method comprising the steps of:
(a) providing a mixed antigen binding construct composition that comprises antigen binding constructs of different sizes; and
(b) separating the mixed antigen binding construct composition based on size; wherein the desired bispecific antigen binding construct comprises
(i) a single domain antibody (VHH) binding region which binds a first target antigen, wherein said single domain antibody binding region is operatively linked to a first IgG Fc domain polypeptide; and
(ii) a Fab portion of a conventional IgG antibody which binds a second target antigen, wherein said Fab portion is operatively linked to a second IgG Fc domain polypeptide; wherein the first and second IgG Fc domain polypeptides dimerize to form the bispecific antigen binding construct.

In an embodiment, the separating based on size comprises size exclusion chromatography.

In an embodiment, the mixed antigen binding construct composition is initially purified by protein A, protein G, protein L, or CH1-selective chromatography.

In another aspect, the present invention provides a method of determining the amount of a desired bispecific antigen binding construct within a mixture of other antigen binding constructs, the method comprising the steps of:
(a) providing a mixed antigen binding construct composition that comprises antigen binding constructs of different sizes; and
(b) separating the mixed antigen binding construct composition based on size; wherein the desired antigen binding construct comprises
(i) a single domain antibody (VHH) binding region which binds a first target antigen, wherein said single domain antibody binding region is operatively linked to a first IgG Fc domain polypeptide; and
(ii) a Fab portion of a conventional IgG antibody which binds a second target antigen, wherein said Fab portion is operatively linked to a second IgG Fc domain polypeptide; wherein the first and second IgG Fc domain polypeptides dimerize to form the bispecific antigen binding construct.

In an embodiment, the separating based on size comprises gel electrophoresis.

In an embodiment, the desired bispecific antigen binding construct is about 100 kDa to about 120 kDa.

In an embodiment, the desired bispecific antigen binding construct is about 112 kDa.

In an embodiment, the other antigen binding constructs are about 75 kDa or about 150 kDa.

BRIEF DESCRIPTION OF THE DRAWINGS

FIG. 2A depicts schematic of a conventional antibody. FIG. 2B depicts schematic of a VHH domain. FIG. 2C depicts schematic of a Fab domain/VHH bispecific antibody of the invention.

FIG. 4 depicts amino acid sequence alignment of representative IgG2 Fc regions. Sequences are as follows: mIgG2aHole, SEQ ID NO: 32; mIgG2aKnob, SEQ ID NO: 33; mFcFusionIgG2aHole, SEQ ID NO: 34; mFcFusionIgG2aKnob, SEQ ID NO: 35; and pUPEX36-mIgG2.P9, SEQ ID NO: 36.

FIG. 5A depicts SDS-PAGE for the antigen binding construct for Target A and Target B. FIG. 5B depicts SDS-PAGE for the antigen binding construct for Target C and Target D.

DETAILED DESCRIPTION OF THE INVENTION

A. Definitions

Figure 1:
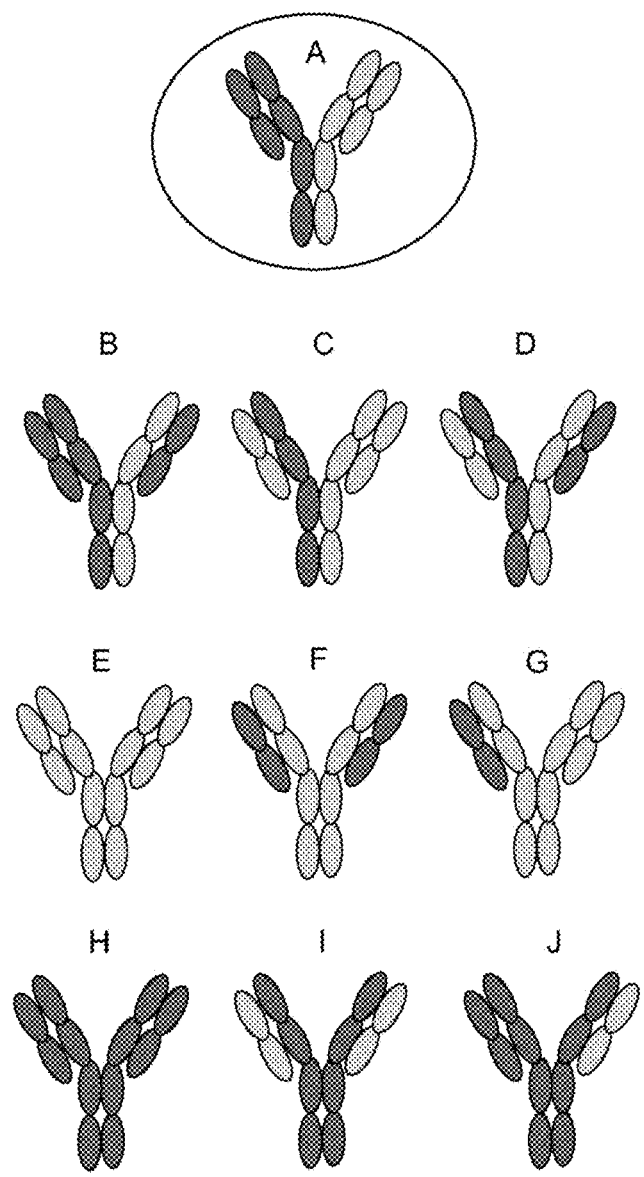
FIG. 1 shows the ten different pairings ((A)-(J)) of heavy and light chain combinations that can result from the production of a bispecific antibody having two distinct heavy chains and two distinct light chains.

"Antibody" or "Immunoglobulin"—As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. a human antigen). "Specificity" for a particular human antigen does not exclude cross-reactivity with species homologues of that antigen. Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody that can be distinguished biochemically. All five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

The light chains of an antibody are classified as either kappa or lambda ($\kappa, \lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, ($\gamma, \mu, \alpha, \delta, \varepsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form the variable region that defines a three-dimensional antigen binding site. This quaternary antibody structure forms the antigen binding site present at the end of each arm of the Y. More specifically, the antigen binding site is defined by three complementary determining regions (CDRs) on each of the VH and VL chains.

"Isolated antibody"—As used herein, an "isolated antibody" is one that has been separated and/or recovered from a component of its natural environment. Contaminant components of its natural environment are materials that would interfere with diagnostic or therapeutic uses of the antibody, and may include enzymes, hormones, and other proteinaceous or non-proteinaceous components. An isolated antibody includes the antibody in situ within recombinant cells since at least one component of the antibody's natural environment will not be present. Ordinarily, however, an isolated antibody will be prepared by at least one purification step.

"Affinity variant"—As used herein, the term "affinity variant" refers to a variant antibody which exhibits one or more changes in amino acid sequence compared to a reference antibody, wherein the affinity variant exhibits an altered affinity for the protein in comparison to the reference antibody. Typically, affinity variants will exhibit an improved affinity for the protein, as compared to the reference antibody. The improvement may be a lower KD, a faster off-rate, or an alteration in the pattern of cross-reactivity with non-human homologues of the protein. Affinity variants typically exhibit one or more changes in amino acid sequence in the CDRs, as compared to the reference antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"Binding site"—As used herein, the term "binding site" comprises a region of a polypeptide which is responsible for selectively binding to a target antigen of interest (e.g. a human antigen). Binding domains comprise at least one binding site. Exemplary binding domains include an antibody variable domain. The antibody molecules of the invention may comprise multiple (e.g., two, three or four) binding sites.

"Camelid-Derived"—In certain preferred embodiments, the antigen binding constructs of the invention comprise framework amino acid sequences and/or CDR amino acid sequences derived from a camelid conventional antibody raised by active immunisation of a camelid. However, antibodies of the invention comprising camelid-derived amino acid sequences may be engineered to comprise framework and/or constant region sequences derived from a human amino acid sequence (i.e. a human antibody) or other non-camelid mammalian species. For example, a human or non-human primate framework region, heavy chain portion, and/or hinge portion may be included in the subject antibodies. In one embodiment, one or more non-camelid amino acids may be present in the framework region of a "camelid-derived" antibody, e.g., a camelid framework amino acid sequence may comprise one or more amino acid mutations in which the corresponding human or non-human primate amino acid residue is present. Moreover, camelid-derived VH and VL domains, or humanised variants thereof, may be linked to the constant domains of human antibodies to produce a chimeric molecule.

"Conservative amino acid substitution"—A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide may be replaced with another amino acid residue from the same side chain family.

"Epitope"—The term "epitope" refers to a specific arrangement of amino acids located on a peptide or protein to which an antibody or antibody fragment binds. Epitopes often consist of a chemically active surface grouping of molecules such as amino acids or sugar side chains, and have specific three-dimensional structural characteristics as well as specific charge characteristics. Epitopes can be linear, i.e., involving binding to a single sequence of amino acids, or conformational, i.e., involving binding to two or more sequences of amino acids in various regions of the antigen that may not necessarily be contiguous.

"Heavy chain portion"—As used herein, the term "heavy chain portion" includes amino acid sequences derived from the constant domains of an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, a binding molecule of the invention may comprise the Fc portion of an immunoglobulin heavy chain (e.g., a hinge portion, a CH2 domain, and a CH3 domain). In another embodiment, a binding molecule of the invention lacks at least a portion of a constant domain (e.g., all or part of a CH2 domain). In certain embodiments, at least one, and prefer-ably all, of the constant domains are derived from a human immunoglobulin heavy chain. For example, in one preferred embodiment, the heavy chain portion comprises a fully human hinge domain. In other preferred embodiments, the heavy chain portion comprises a fully human Fc portion (e.g., hinge, CH2 and CH3 domain sequences from a human immunoglobulin).

In certain embodiments, the constituent constant domains of the heavy chain portion are from different immunoglobulin molecules. For example, a heavy chain portion of a polypeptide may comprise a CH2 domain derived from an IgG1 molecule and a hinge region derived from an IgG3 or IgG4 molecule. In other embodiments, the constant domains are chimeric domains comprising portions of different immunoglobulin molecules. For example, a hinge may comprise a first portion from an IgG1 molecule and a second portion from an IgG3 or IgG4 molecule. As set forth above, it will be understood by one of ordinary skill in the art that the constant domains of the heavy chain portion may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant domain (CL). Exemplary modifications include additions, deletions or substitutions of one or more amino acids in one or more domains.

"Variable region" or "variable domain"—The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site.

The first, second and third hypervariable loops of the Vλ light chain domain are referred to herein as L1(λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20:267-279 (2000)). The first, second and third hypervariable loops of the Vκ light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20:267-279 (2000)).

Unless otherwise indicated, the terms L1, L2 and L3 respectively refer to the first, second and third hypervariable loops of a VL domain, and encompass hypervariable loops obtained from both Vκ and Vλ isotypes. The terms H1, H2 and H3 respectively refer to the first, second and third hypervariable loops of the VH domain, and encompass hypervariable loops obtained from any of the known heavy chain isotypes, including γ, ε, δ, α or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, MD, 1983) and the limits of the HVs and the CDRs may be different in some VH and VL domains.

The CDRs of the VL and VH domains can typically be defined as comprising the following amino acids: residues 24-34 (CDRL1), 50-56 (CDRL2) and 89-97 (CDRL3) in the light chain variable domain, and residues 31-35 or 31-35b (CDRH1), 50-65 (CDRH2) and 95-102 (CDRH3) in the heavy chain variable domain; (Kabat et al., Sequences of Proteins of Immunological Interest, 5th Ed. Public Health Service, National Institutes of Health, Bethesda, MMD (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"CDR"—As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra Amino acid residues of a VHH domain are numbered according to the general numbering for a VH domain given by Kabat et al. It should be noted that, as is well known in the art for VH domains and for VHH domains, the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Details on VHH domain numbering are described in U.S. Pat. No. 8,703,131, which is incorporated by reference herein.

"Framework region"—The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three-dimensional configuration in an aqueous environment. The remainder of the heavy and light variable domains show less inter-molecular variability in amino acid sequence and are termed the framework regions. The framework regions largely adopt a μ-sheet conformation and the CDRs form loops which connect, and in some cases form part of, the μ-sheet structure. Thus, these framework regions act to form a scaffold that provides for positioning the six CDRs in correct orientation by inter-chain, non-covalent interactions.

The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Hinge region"—As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161: 4083 (1998)). Antibodies comprising a "fully human" hinge region may contain one of the hinge region sequences shown in Table 2 below.

TABLE 2

Human hinge sequences

| IgG | Upper hinge | Middle hinge | Lower hinge |
|---|---|---|---|
| IgG1 | EPKSCDKTHT (SEQ ID NO: 1) | CPPCP (SEQ ID NO: 2) | APELLGGP (SEQ ID NO: 3) |
| IgG2 | ERK | CCVECPPPCP (SEQ ID NO: 4) | APPVAGP (SEQ ID NO: 5) |
| IgG3 | ELKTPLGDTTHT (SEQ ID NO: 6) | CPRCP-(EPKSCDTPPCPRCP)$_3$ (SEQ ID NO: 7) | APELLGGP (SEQ ID NO: 3) |
| IgG4 | ESKYGPP (SEQ ID NO: 8) | CPSCP (SEQ ID NO: 9) | APEFLGGP (SEQ ID NO: 10) |

"Fragment"—The term "fragment" refers to a part or portion of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to a human antigen). As used herein, the term "fragment" of an antibody molecule includes antigen-binding fragments of antibodies, for example, an antibody light chain (VL), an antibody heavy chain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

"Specificity"—The term "specificity" refers to the ability to specifically bind (e.g., immunoreact with) a given target antigen, e.g., a human target antigen. An antibody or antigen binding fragment thereof may be monospecific and contain one or more binding sites which specifically bind a target, or an antibody or antigen binding fragment thereof may be multispecific and contain two or more binding sites which specifically bind the same or different targets. In certain embodiments, an antigen binding construct of the invention is specific for more than one target antigen. In certain embodiments, an antigen binding construct of the invention is specific for two target antigens. In certain embodiments, an antigen binding construct of the invention is specific for more than one human target antigen. In certain embodiments, an antigen binding construct of the invention is specific for two human target antigens. For example, in one embodiment, a bispecific binding molecule of the invention binds to Target Antigen A (Target A) and Target Antigen B (Target B). As another example, in one embodiment, a bispecific binding molecule of the invention binds to Target Antigen C (Target C) and Target Antigen D (Target D).

"Synthetic"—As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

"Engineered"—As used herein the term "engineered" includes manipulation of nucleic acid or polypeptide molecules by synthetic means (e.g., by recombinant techniques, in vitro peptide synthesis, by enzymatic or chemical coupling of peptides, or some combination of these techniques). Preferably, the antigen binding constructs of the invention are engineered, including for example, humanized and/or chimeric antibodies, and antibodies which have been engineered to improve one or more properties, such as antigen binding, stability/half-life or effector function.

"Fc region"—As used herein, the term "Fc region" refers to the portion of a native immunoglobulin formed by the Fc domains of its two heavy chains. A native Fc region is homodimeric. As used herein, the term "variant Fc region" refers to an Fc region with one or more alterations relative to a native Fc region. An Fc region may be altered by amino acid substitutions, additions and/or deletions, linkage of additional moieties, and/or alteration of the native glycans. The term encompasses Fc regions wherein each of the constituent Fc domains is different. Examples of heterodimeric Fc regions include, without limitation, Fc regions made using the "knobs into holes" technology as described in, for example U.S. Pat. No. 8,216,805. The term also encompasses single chain Fc regions where the constituent Fc domains are linked together by a linker moiety, as described in, for example, US Patent Application Publication Nos. 2009/0252729 A1 and US 2011/0081345 A1. Unless otherwise stated, all antibody constant region numbering refers to the EU numbering scheme, as described in Edelman et al., Proc. Natl. Acad. Sci. USA 63(1): 78-85 (1969).

"Humanising substitutions"—As used herein, the term "humanising substitutions" refers to amino acid substitutions in which the amino acid residue present at a particular position in the VH or VL domain antibody (for example a camelid-derived antibody) is replaced with an amino acid residue which occurs at an equivalent position in a reference human VH or VL domain. The reference human VH or VL domain may be a VH or VL domain encoded by the human germline. Humanising substitutions may be made in the framework regions and/or the CDRs of an antibody, defined herein.

"Humanised antibody or variant"—As used herein the term "humanised antibody" or "humanised variant" refers to a variant antibody which contains one or more "humanising substitutions" compared to a reference antibody, wherein a portion of the reference antibody (e.g. the VH domain and/or the VL domain or parts thereof containing at least one CDR) has an amino acid derived from a non-human species, and the "humanising substitutions" occur within the amino acid sequence derived from a non-human species.

"Heavy-chain-only antibody" or "VHH antibody"—As used herein, the term "heavy-chain-only antibody" or "VHH antibody" refers to a second type of antibody produced only by species of the Camelidae family, which includes camels, llama, alpaca. Heavy chain-only antibodies are composed of two heavy chains and are devoid of light chains. Each heavy chain has a variable domain at the N-terminus, and these variable domains are referred to as "VHH" domains in order to distinguish them from the variable domains of the heavy chains of the conventional heterotetrameric antibodies, i.e., the VH domains described above.

"Modified antibody"—As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

The term "modified antibody" may also be used herein to refer to amino acid sequence variants of an antibody. It will be understood by one of ordinary skill in the art that an antibody may be modified to produce a variant antibody which varies in amino acid sequence in comparison to the antibody from which it was derived. For example, nucleotide or amino acid substitutions leading to conservative substitutions or changes at "non-essential" amino acid residues may be made (e.g., in CDR and/or framework residues). Amino acid substitutions can include replacement of one or more amino acids with a naturally occurring or non-natural amino acid.

"Target A"—As used herein, the term "Target A" or "Target Antigen A" refers to a target antigen that the conventional Fab-containing portion of the antibody of the invention has binding specificity for.

"Target B"—As used herein, the term "Target B" or "Target Antigen B" refers to a target antigen that the VHH-containing portion of the antibody of the invention has binding specificity for. Target A and Target B may form a complex together. In certain embodiments, the bispecific antibody of the invention with specificity to Target A and Target B may also bind the complex of Target A and Target B.

"Target C"—As used herein, the term "Target C" or "Target Antigen C" refers to a target antigen that the conventional Fab-containing portion of the antibody of the invention has binding specificity for.

"Target D"—As used herein, the term "Target D" or "Target Antigen D" refers to a target antigen that the VHH-containing portion of the antibody of the invention has binding specificity for.

"Antigen binding construct"—As used herein, the term "antigen binding construct" comprises a single domain antibody (VHH) binding region fused to an IgG Fc domain portion; a heavy chain-Fc domain portion of a conventional IgG antibody; and a light chain portion of the conventional IgG antibody. The VHH binding region is an antibody fragment consisting of a single monomeric variable antibody domain. It selectively binds a specific first antigen. The heavy chain-Fc domain portion of a conventional IgG antibody includes the variable and constant domains of a conventional IgG heavy chain. The light chain portion of a conventional IgG antibody includes the variable and constant domains of a conventional IgG light chain. The heavy chain and light chain portion of the conventional IgG antibody selectively bind a specific second antigen.

B. Multispecific Antigen Binding Construct

One component of the multispecific antigen binding construct of the present invention is a heavy and light chain of a conventional antibody or antigen binding fragment thereof, wherein the term "conventional antibody" is used herein to describe heterotetrameric antibodies containing heavy and light immunoglobulin chains arranged according to the "Y" configuration shown in FIG. 1. Such conventional antibodies may derive from any suitable species including but not limited to antibodies of llama, mouse, rat, rabbit, goat, hamster, chicken, monkey or human origin.

In certain exemplary embodiments, the conventional antibody is a SIMPLE antibody as described and claimed in, e.g., U.S. Pat. No. 8,524,231, the entire content of which is incorporated herein by reference. SIMPLE antibodies may comprise a heavy chain variable domain (VH) and a light chain variable domain (VL) wherein the VH and/or VL domains or one or more complementarity determining regions (CDRs) thereof are derived from an animal of the Camelidae family, i.e. derived from conventional antibodies raised by immunisation of camelids (e.g., llama). The antibodies or antigen binding fragments exhibiting high human homology or having at least one camelid-derived CDR sequence, VH and/or VL domain may be humanised or germlined variants of VH or VL domains from camelid conventional antibodies, wherein the terms "humanised" and "germlined" are as defined elsewhere herein.

In certain embodiments, the conventional antibody antigen binding region may be referred to as a "Fab" (Fragment antigen-binding). The Fab comprises one constant domain and one variable domain from each of the heavy chain and light chain. The variable heavy and light chains contain the CDRs responsible for antigen binding. The Fab portion of a conventional antibody is found in the schematic of FIGS. 2A and 2C.

Another component of the multispecific antigen binding construct of the present invention comprises a VHH domain or heavy chain of a VHH antibody or Nanobody. VHH antibodies, which are camelid-derived heavy chain antibodies, are composed of two heavy chains and are devoid of light chains (Hamers-Casterman et al., Nature. 1993; 363; 446-8). Each heavy chain of the VHH antibody has a variable domain at the N-terminus, and these variable domains are referred to in the art as "VHH" domains in order to distinguish them from the variable domains of the heavy chains of the conventional antibodies i.e. the VH domains. Similar to conventional antibodies, the VHH domains of the molecule confer antigen binding specificity, and therefore VHH antibodies or fragments such as isolated VHH domains are suitable as components of the antigen binding construct of the present disclosure.

For the multispecific antigen binding construct of the present disclosure, the conventional heterotetrameric antibodies or VHH antibodies specific for their respective selective target antigen may be generated or obtained by active immunization of a host species with a polypeptide comprising that antigen. For the production of conventional antibodies, the host species may be selected from any of the following: mouse, rat, rabbit, goat, hamster, chicken, monkey, or species of the family Camelidae. For the production of VHH antibodies, any species from the family Camelidae, including lama species, may be immunized with a polypeptide including the respective antigen.

Exemplary antigen-binding constructs of the present invention are shown below.

TABLE 3

Antigen-binding construct sequences for Target A/Target B antibodies. HCDR1-HCDR3 and LCDR1-LCDR3, according to Kabat numbering, are bold.

| Sequence ID | Sequence |
|---|---|
| mIgG2aHole | CGTTTAAACGGTACCGCCGCCACCATGGGCTGGTCCTGCATCAT<br>CCTGTTTCTGGTGGCCACCGCCACAGGCGTCCACTCTGGAGAC<br>GCCAATCCTTCACTCGAATTCCGTCTCGCTAAAACAACAGCCCC<br>ATCGGTCTATCCACTGGCCCCTGTGTGTGGAGATACAACTGGCT<br>CCTCGGTGACTCTAGGATGCCTGGTCAAGGGTTATTTCCCTGAG<br>CCAGTGACCTTGACCTGGAACTCTGGATCCCTGTCCAGTGGTGT<br>GCACACCTTCCCAGCTGTCCTGCAGTCTGACCTCTACACCCTCA<br>GCAGCTCAGTGACTGTAACCTCGAGCACCTGGCCCAGCCAGTC<br>CATCACCTGCAATGTGGCCCACCCGGCAAGCAGCACCAAGGTG<br>GACAAGAAAATTGAGCCCAGAGGGCCCACAATCAAGCCCTGTC<br>CTCCATGCAAATGCCCAGCACCTAACCTCTTGGGTGGACCAGAC<br>GTCTTCATCTTCCCTCCAAAGATCAAGGATGTACTCATGATCTCC<br>CTGAGCCCCATAGTCACATGTGTGGTGGTGGATGTGAGCGAGG<br>ATGACCCAGATGTCCAGATCAGCTGGTTTGTGAACAACGTGGAA<br>GTACACACAGCTCAGACACAAACCCATAGAGAGGATTACCAGAG<br>TACTCTCCGGGTGGTCAGTGCCCTCCCCATCCAGCACCAGGAC<br>TGGATGAGTGGCAAGGAGTTCAAATGCAAGGTCAACAACAAGA<br>CCTCCCAGCGCCCGAAGAGAGAACCATCTCAAAACCCAAAGGG<br>TCAGTAAGAGCTCCACAGGTATATGTCTTGCCTCCACCAGAAGA<br>AGAGATGACTAAGAAACAGGTCACTCTGTCCTGCGCTGTCACAG<br>ACTTCATGCCTGAAGACATTTACGTGGAGTGGACCAACAACGGG<br>AAAACAGAGCTAAACTACAAGAACACTGAACCAGTCCTGGACTC<br>TGATGGTTCTTACTTCATGGTGAGCAAGCTGAGAGTGGAAAAGA<br>AGAACTGGGTGGAAAGAAATAGCTACTCCTGTTCAGTGGTCCAC<br>GAGGGTCTGCACAATCACCACACGACTAAGAGCTTCTCCCGGAC<br>TCCGGGTAAA<br>(SEQ ID NO: 17) |
| mIgG2aHole Amino acid sequence | RLNGTAATMGWSCIILFLVATATGVHSGDANPSLEFRLAKTTAPSVY<br>PLAPVCGDTTGSSVTLGCLVKGYFPEPVTLTWNSGSLSSGVHTFPA<br>VLQSDLYTLSSSVTVTSSTWPSQSITCNVAHPASSTKVDKKIEPRGP<br>TIKPCPPCKCPAPNLLGGPDVFIFPPKIKDVLMISLSPIVTCVVVDVSE<br>DDPDVQISWFVNNVEVHTAQTQTHREDYQSTLRVVSALPIQHQDW<br>MSGKEFKCKVNNKDLPAPEERTISKPKGSVRAPQVYVLPPPEEEMT<br>KKQVTLSCAVTDFMPEDIYVEWTNNGKTELNYKNTEPVLDSDGSYF<br>MVSKLRVEKKNWVERNSYSCSVVHEGLHNHHTTKSFSRTPGK<br>(SEQ ID NO: 18) |
| mIgG2aKnob | CGTTTAAACGGTACCGCCGCCACCATGGGCTGGTCCTGCATCAT<br>CCTGTTTCTGGTGGCCACCGCCACAGGCGTCCACTCTGGAGAC<br>GCCAATCCTTCACTCGAATTCCGTCTCGCTAAAACAACAGCCCC<br>ATCGGTCTATCCACTGGCCCCTGTGTGTGGAGATACAACTGGCT<br>CCTCGGTGACTCTAGGATGCCTGGTCAAGGGTTATTTCCCTGAG<br>CCAGTGACCTTGACCTGGAACTCTGGATCCCTGTCCAGTGGTGT<br>GCACACCTTCCCAGCTGTCCTGCAGTCTGACCTCTACACCCTCA<br>GCAGCTCAGTGACTGTAACCTCGAGCACCTGGCCCAGCCAGTC<br>CATCACCTGCAATGTGGCCCACCCGGCAAGCAGCACCAAGGTG<br>GACAAGAAAATTGAGCCCAGAGGGCCCACAATCAAGCCCTGTC<br>CTCCATGCAAATGCCCAGCACCTAACCTCTTGGGTGGACCAGAC<br>GTCTTCATCTTCCCTCCAAAGATCAAGGATGTACTCATGATCTCC<br>CTGAGCCCCATAGTCACATGTGTGGTGGTGGATGTGAGCGAGG<br>ATGACCCAGATGTCCAGATCAGCTGGTTTGTGAACAACGTGGAA<br>GTACACACAGCTCAGACACAAACCCATAGAGAGGATTACAACAG<br>TACTCTCCGGGTGGTCAGTGCCCTCCCCATCCAGCACCAGGAC<br>TGGATGAGTGGCAAGGAGTTCAAATGCAAGGTCAACAACAAAGA<br>CCTCCCAGCGCCCGAAGAGAGAACCATCTCAAAACCCAAAGGG<br>TCAGTAAGAGCTCCACAGGTATATGTCTTGCCTCCACCAGAAGA<br>AGAGATGACTAAGAAACAGGTCACTCTGTGGTGCATGGTCACAG<br>ACTTCATGCCTGAAGACATTTACGTGGAGTGGACCAACAACGGG<br>AAAACAGAGCTAAACTACAAGAACACTGAACCAGTCCTGGACTC<br>TGATGGTTCTTACTTCATGTACAGCAAGCTGAGAGTGGAAAAGA<br>AGAACTGGGTGGAAAGAAATAGCTACTCCTGTTCAGTGGTCCAC<br>GAGGGTCTGCACAATCACCACACGACTAAGAGCTTCTCCCGGAC<br>TCCGGGTAAA<br>(SEQ ID NO: 19) |

TABLE 3-continued

Antigen-binding construct sequences for Target A/Target B antibodies. HCDR1-HCDR3 and LCDR1-LCDR3, according to Kabat numbering, are bold.

| Sequence ID | Sequence |
| --- | --- |
| mIgG2aKnob Amino acid sequence | RLNGTAATMGWSCIILFLVATATGVHSGDANPSLEFRLAKTTAPSVY PLAPVCGDTTGSSVTLGCLVKGYFPEPVTLTWNSGSLSSGVHTFPA VLQSDLYTLSSSVTVTSSTWPSQSITCNVAHPASSTKVDKKIEPRGP TIKPCPPCKCPAPNLLGGPDVFIFPPKIKDVLMISLSPIVTCVVVDVSE DDPDVQISWFVNNVEVHTAQTQTHREDYNSTLRVVSALPIQHQDW MSGKEFKCKVNNKDLPAPEERTISKPKGSVRAPQVYVLPPPEEEMT KKQVTLWCMVTDFMPEDIYVEWTNNGKTELNYKNTEPVLDSDGSY FMYSKLRVEKKNWVERNSYSCSVVHEGLHNHHTTKSFSRTPGK (SEQ ID NO: 20) |
| mFcFusionIg G2aHole | CGTTTAAACGGTACCGCCGCCACCATGGGCTGGTCCTGCATCAT CCTGTTTCTGGTGGCCACCGCCACAGGCGTCCACTCTGGAGAC GCCAATCCTTCACTCGAATTCCGTCTCGAGCCCAGAGGGCCCAC AATCAAGCCCTGTCCTCCATGCAAATGCCCAGCACCTAACCTCT TGGGTGGACCAGACGTCTTCATCTTCCCTCCAAAGATCAAGGAT GTACTCATGATCTCCCTGAGCCCCATAGTCACATGTGTGGTGGT GGATGTGAGCGAGGATGACCCAGATGTCCAGATCAGCTGGTTT GTGAACAACGTGGAAGTACACACAGCTCAGACACAAACCCATAG AGAGGATTACAACAGTACTCTCCGGGTGGTCAGTGCCCTCCCCA TCCAGCACCAGGACTGGATGAGTGGCAAGGAGTTCAAATGCAA GGTCAACAACAAAGACCTCCCAGCGCCCGAAGAGAGAACCATC TCAAAACCCAAAGGGTCAGTAAGAGCTCCACAGGTATATGTCTT GCCTCCACCAGAAGAAGAGATGACTAAGAAACAGGTCACTCTGT CCTGCGCTGTCACAGACTTCATGCCTGAAGACATTTACGTGGAG TGGACCAACAACGGGAAAACAGAGCTAAACTACAAGAACACTGA ACCAGTCCTGGACTCTGATGGTTCTTACTTCATGGTGAGCAAGC TGAGAGTGGAAAAGAAGAACTGGGTGGAAAGAAATAGCTACTCC TGTTCAGTGGTCCACGAGGGTCTGCACAATCACCACACGACTAA GAGCTTCTCCCGGACTCCGGGTAAA (SEQ ID NO: 21) |
| mFcFusionIg G2aHole Amino acid sequence | RLNGTAATMGWSCIILFLVATATGVHSGDANPSLEFRLEPRGPTIKP CPPCKCPAPNLLGGPDVFIFPPKIKDVLMISLSPIVTCVVVDVSEDDP DVQISWFVNNVEVHTAQTQTHREDYNSTLRVVSALPIQHQDWMSG KEFKCKVNNKDLPAPEERTISKPKGSVRAPQVYVLPPPEEEMTKKQ VTLSCAVTDFMPEDIYVEWTNNGKTELNYKNTEPVLDSDGSYFMVS KLRVEKKNWVERNSYSCSVVHEGLHNHHTTKSFSRTPGK (SEQ ID NO: 22) |
| mFcFusionIg G2aKnob | CGTTTAAACGGTACCGCCGCCACCATGGGCTGGTCCTGCATCAT CCTGTTTCTGGTGGCCACCGCCACAGGCGTCCACTCTGGAGAC GCCAATCCTTCACTCGAATTCCGTCTCGAGCCCAGAGGGCCCAC AATCAAGCCCTGTCCTCCATGCAAATGCCCAGCACCTAACCTCT TGGGTGGACCAGACGTCTTCATCTTCCCTCCAAAGATCAAGGAT GTACTCATGATCTCCCTGAGCCCCATAGTCACATGTGTGGTGGT GGATGTGAGCGAGGATGACCCAGATGTCCAGATCAGCTGGTTT GTGAACAACGTGGAAGTACACACAGCTCAGACACAAACCCATAG AGAGGATTACAACAGTACTCTCCGGGTGGTCAGTGCCCTCCCCA TCCAGCACCAGGACTGGATGAGTGGCAAGGAGTTCAAATGCAA GGTCAACAACAAAGACCTCCCAGCGCCCGAAGAGAGAACCATC TCAAAACCCAAAGGGTCAGTAAGAGCTCCACAGGTATATGTCTT GCCTCCACCAGAAGAAGAGATGACTAAGAAACAGGTCACTCTGT GGTGCATGGTCACAGACTTCATGCCTGAAGACATTTACGTGGAG TGGACCAACAACGGGAAAACAGAGCTAAACTACAAGAACACTGA ACCAGTCCTGGACTCTGATGGTTCTTACTTCATGTACAGCAAGCT GAGAGTGGAAAAGAAGAACTGGGTGGAAAGAAATAGCTACTCCT GTTCAGTGGTCCACGAGGGTCTGCACAATCACCACACGACTAAG AGCTTCTCCCGGACTCCGGGTAAA (SEQ ID NO: 23) |
| mFcFusionIg G2aKnob Amino acid sequence | RLNGTAATMGWSCIILFLVATATGVHSGDANPSLEFRLEPRGPTIKP CPPCKCPAPNLLGGPDVFIFPPKIKDVLMISLSPIVTCVVVDVSEDDP DVQISWFVNNVEVHTAQTQTHREDYNSTLRVVSALPIQHQDWMSG KEFKCKVNNKDLPAPEERTISKPKGSVRAPQVYVLPPPEEEMTKKQ VTLWCMVTDFMPEDIYVEWTNNGKTELNYKNTEPVLDSDGSYFMY SKLRVEKKNWVERNSYSCSVVHEGLHNHHTTKSFSRTPGK (SEQ ID NO: 24) |
| pUPEX36-mIgG2.P90 | AGTTTAAACGGTACCGCCGCCACCATGGGCTGGTCCTGCATCAT CCTGTTTCTGGTGGCCACCGCCACAGGCGTCCACTCTGGAGAC GCCTCCTTAACACTCGAATTCCGTCTCGCTAAAACAACAGCCCC ATCGGTCTATCCACTGGCCCCTGTGTGTGGAGATACAACTGGCT CCTCGGTGACTCTAGGATGCCTGGTCAAGGGTTATTTCCCTGAG CCAGTGACCTTGACCTGGAACTCTGGATCCCTGTCCAGTGGTGT |

TABLE 3-continued

Antigen-binding construct sequences for Target A/Target B antibodies. HCDR1-HCDR3 and LCDR1-LCDR3, according to Kabat numbering, are bold.

| Sequence ID | Sequence |
|---|---|
| | GCACACCTTCCCAGCTGTCCTGCAGTCTGACCTCTACACCCTCA<br>GCAGCTCAGTGACTGTAACCTCGAGCACCTGGCCCAGCCAGTC<br>CATCACCTGCAATGTGGCCCACCCGGCAAGCAGCACCAAGGTG<br>GACAAGAAAATTGAGCCCAGAGGGCCCACAATCAAGCCCTGTC<br>CTCCATGCAAATGCCCAGCACCTAACCTCTTGGGTGGACCATCC<br>GTCTTCATCTTCCCTCCAAAGATCAAGGATGTACTCATGATCTCC<br>CTGAGCCCCATAGTCACATGTGTGGTGGTGGATGTGAGCGAGG<br>ATGACCCAGATGTCCAGATCAGCTGGTTTGTGAACAACGTGGAA<br>GTACACACAGCTCAGACACAAACCCATAGAGAGGATTACAACAG<br>TACTCTCCGGGTGGTCAGTGCCCTCCCCATCCAGCACCAGGAC<br>TGGATGAGTGGCAAGGAGTTCAAATGCAAGGTCAACAACAAAGA<br>CCTCCCAGCGCCCATCGAGAGAACCATCTCAAAACCCAAAGGGT<br>CAGTAAGAGCTCCACAGGTATATGTCTTGCCTCCACCAGAAGAA<br>GAGATGACTAAGAAACAGGTCACTCTGACCTGCATGGTCACAGA<br>CTTCATGCCTGAAGACATTTACGTGGAGTGGACCAACAACGGGA<br>AAACAGAGCTAAACTACAAGAACACTGAACCAGTCCTGGACTCT<br>GATGGTTCTTACTTCATGTACAGCAAGC<br>(SEQ ID NO: 25) |
| pUPEX36-<br>mIgG2.P90<br>Amino acid<br>sequence | SLNGTAATMGWSCIILFLVATATGVHSGDASLTLEFRLAKTTAPSVY<br>PLAPVCGDTTGSSVTLGCLVKGYFPEPVTLTWNSGSLSSGVHTFPA<br>VLQSDLYTLSSSVTVTSSTWPSQSITCNVAHPASSTKVDKKIEPRGP<br>TIKPCPPCKCPAPNLLGGPSVFIFPPKIKDVLMISLSPIVTCVVVDVSE<br>DDPDVQISWFVNNVEVHTAQTQTHREDYNSTLRVVSALPIQHQDW<br>MSGKEFKCKVNNKDLPAPIERTISKPKGSVRAPQVYVLPPPEEEMT<br>KKQVTLTCMVTDFMPEDIYVEWTNNGKTELNYKNTEPVLDSDGSYFMYSK<br>(SEQ ID NO: 26) |
| Target A -<br>mIgG2a-Hole<br>Amino acid<br>sequence | AKTTAPSVYPLAPVCGDTTGSSVTLGCLVKGYFPEPVTLTWNSGSL<br>SSGVHTFPAVLQSDLYTLSSSVTVTSSTWPSQSITCNVAHPASSTK<br>VDKKIEPRGPTIKPCPPCKCPAPNLLGGPDVFIFPPKIKDVLMISLSPI<br>VTCVVVDVSEDDPDVQISWFVNNVEVHTAQTQTHREDYQSTLRVV<br>SALPIQHQDWMSGKEFKCKVNNKDLPAPEERTISKPKGSVRAPQ<br>YVLPPPEEEMTKKQVTLSCAVTDFMPEDIYVEWTNNGKTELNYKNT<br>EPVLDSDGSYFMVSKLRVEKKNWVERNSYSCSVVHEGLHNHHTTKSFSRTPGK<br>(SEQ ID NO: 27) |
| Target B -<br>mIgG2a_FC-<br>fusion-Knob<br>Amino acid<br>sequence | EPRGPTIKPCPPCKCPAPNLLGGPDVFIFPPKIKDVLMISLSPIVTCV<br>VVDVSEDDPDVQISWFVNNVEVHTAQTQTHREDYNSTLRVVNSALPI<br>QHQDWMSGKEFKCKVNNKDLPAPEERTISKPKGSVRAPQVYVLPP<br>PEEEMTKKQVTLWCMVTDFMPEDIYVEWTNNGKTELNYKNTEPVL<br>DSDGSYFMYSKLRVEKKNWVERNSYSCSVVHEGLHNHHTTKSFSRTPGK<br>(SEQ ID NO: 28) |

TABLE 4

Antigen-binding construct sequences for Target C/Target D antibodies.

| Sequence ID | Sequence GGGGSGGGGS linker bold italic;<br>Fc dead aglycosylated N297A mutation bold;<br>Fc knob mutation (T366W) and hole mutations<br>(T366S/L368A/Y407V) underlined and bold |
|---|---|
| Anti-Target D<br>VHH2H3-<br>mFc<br>Dead_Knob<br>(T366W) | GGGGSGGGGSEPRGPTIKPCPPCKCPAPNLLGGPSVFIFPPKIKDV<br>LMISLSPIVTCVVVDVSEDDPDVQISWFVNNVEVHTAQTQTHREDY<br>ASTLRVVSALPIQHQDWMSGKEFKCKVNNKDLPAPIERTISKPKGS<br>VRAPQVYVLPPPEEEMTKKQVTLWCMVTDFMPEDIYVEWTNNGKT<br>ELNYKNTEPVLDSDGSYFMYSKLRVEKKNWVERNSYSCSVVHEGL<br>HNHHTTKSFSRTPG<br>(SEQ ID NO: 29) |
| Anti-Target D<br>VHH3H2-<br>mFc<br>Dead_Knob<br>(T366W) | GGGGSGGGGSEPRGPTIKPCPPCKCPAPNLLGGPSVFIFPPKIKDV<br>LMISLSPIVTCVVVDVSEDDPDVQISWFVNNVEVHTAQTQTHREDY<br>ASTLRVVSALPIQHQDWMSGKEFKCKVNNKDLPAPIERTISKPKGS<br>VRAPQVYVLPPPEEEMTKKQVTLWCMVTDFMPEDIYVEWTNNGKT<br>ELNYKNTEPVLDSDGSYFMYSKLRVEKKNWVERNSYSCSVVHEGL<br>HNHHTTKSFSRTPG<br>(SEQ ID NO: 30) |

TABLE 4-continued

Antigen-binding construct sequences for
Target C/Target D antibodies.

| Sequence ID | Sequence GGGGSGGGGS linker bold italic;<br>Fc dead aglycosylated N297A mutation bold;<br>Fc knob mutation (T366W) and hole mutations<br>(T366S/L368A/Y407V) underlined and bold |
|---|---|
| 4R36B7-<br>mIgG2a<br>Dead_Hole<br>(T366S/L368<br>A/Y407V) | AKTTAPSVYPLAPVCGDTTGSSVTLGCLVKGYFPEPVTLTWN<br>SGSLSSGVHTFPAVLQSDLYTLSSSVTVTSSTWPSQSITCNV<br>AHPASSTKVDKKIEPRGPTIKPCPPCKCPAPNLLGGPSVFIFP<br>PKIKDVLMISLSPIVTCVVVDVSEDDPDVQISWFVNNVEVHTA<br>QTQTHREDYASTLRVVSALPIQHQDWMSGKEFKCKVNNKDL<br>PAPIERTISKPKGSVRAPQVYVLPPPEEEMTKKQVTLSCAVTD<br>FMPEDIYVEWTNNGKTELNYKNTEPVLDSDGSYFMVSKLRVE<br>KKNWVERNSYSCSVVHEGLHNHHTTKSFSRTPGK<br>(SEQ ID NO: 31) |

C. Dimerization of VHH and Conventional Antibody

The present invention overcomes the problems of chain mispairing that exist with traditional bispecific antibody formats. For example, traditional bispecific antibody chain pairing can lead to up ten different antibody species (FIG. 1). With ten different possible options, yield of the desired bispecific antibody is generally low and isolating the desired bispecific antibody from the population of other antibodies is difficult. In some instances, this issue can be partially overcome by the use of heterodimerization methods that force certain desired configurations. For example, the heterodimerization methods described below force specific Fc domain interactions, resulting in one of four possible configurations (FIG. 1 (A)-(D)). Unfortunately, however, these heterodimerization methods still allow for random pairing of the light chains and prevent uniform generation of a bispecific antibody with a single configuration.

Figure 2C:
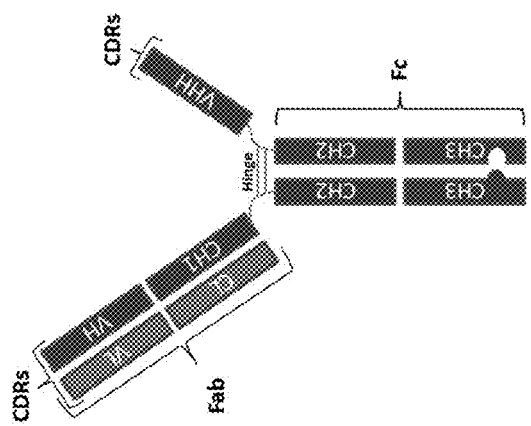
FIGS. 2A-2C depict antigen binding construct schematics.
Figure 2B:
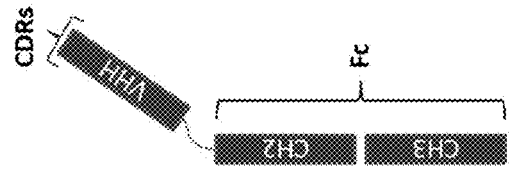
Figure 2A:
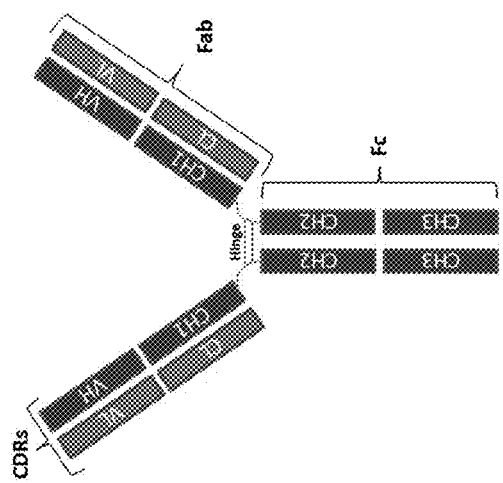
Figure 3:
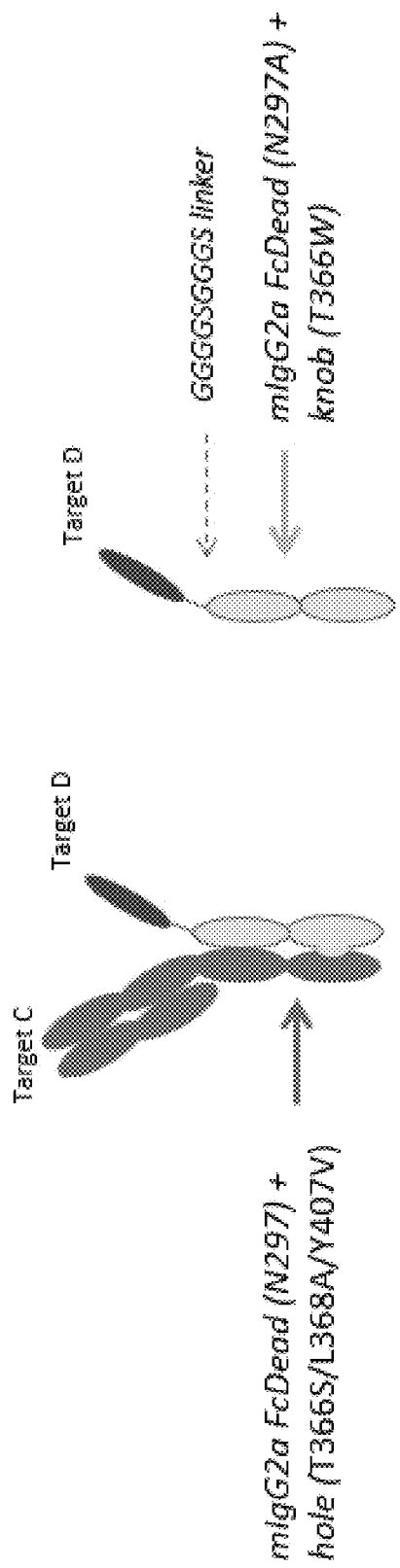
FIG. 3 depicts antigen binding construct schematic of a bispecific antibody with knob-into-hole Fc mutations and an Fc dead aglycosylation N297A mutation in both Fc portions. The conventional Fab portion contains hole mutations and a VHH portion contains a knob T366W mutation.

To overcome this deficiency in the art, the multispecific antigen binding constructs of the present invention comprise a single VHH binding region which binds a first target antigen, wherein said VHH binding region is operatively linked to a first IgG Fc domain polypeptide, and a Fab portion of a conventional IgG antibody which binds a second target antigen, wherein said Fab portion is operatively linked to a second IgG Fc domain polypeptide, and wherein the first and second IgG Fc domain polypeptides dimerize to form the bispecific antigen binding construct (FIG. 2C). The light chain portion of the Fab is only able to pair with the heavy chain portion of the Fab. Accordingly, this ensures that only the desired bispecific configuration is obtained.

In an aspect of the invention, the two Fc domains of the antigen binding construct are heterodimerized through knobs-into-holes pairing. This dimerization technique utilizes protuberances ("knobs") and cavities ("holes") engineered into the interface of CH3 domains. Where a suitably positioned and dimensioned knob or hole exists at the interface of either the first or second CH3 domain, it is only necessary to engineer a corresponding hole or knob, respectively, at the adjacent interface, thus promoting and strengthening Fc domain pairing in the CH3/CH3 domain interface. The IgG Fc domain that is fused to the VHH is provided with a knob, and the IgG Fc domain of the conventional antibody is provided with a hole designed to accommodate the knob, or vice-versa. A "knob" refers to an at least one amino acid side chain, typically a larger side chain, that protrudes from the interface of the CH3 portion of a first Fc domain. The protrusion creates a "knob" which is complementary to and received by a "hole" in the CH3 portion of a second Fc domain. The "hole" is an at least one amino acid side chain, typically a smaller side chain, which recedes from the interface of the CH3 portion of the second Fc domain. This technology is described, for example, in U.S. Pat. No. 5,821,333; Ridgway et al., Protein Engineering 9:617-621 (1996); and Carter P., J. Immunol. Methods 248: 7-15 (2001).

Exemplary amino acid residues that may act as a knob include arginine (R), phenylalanine (F), tyrosine (Y), and tryptophan (W). An existing amino acid residue in the CH3 domain may be replaced or substituted with a knob amino acid residue. Preferred amino acids to be substituted may include any amino acid with a small side chain, such as alanine (A), asparagine (N), aspartic acid (D), glycine (G), serine (S), threonine (T), or valine (V).

Exemplary amino acid residues that may act as a hole include alanine (A), serine (S), threonine (T), and valine (V). An existing amino acid residue in the CH3 domain may be replaced or substituted with a hole amino acid residue. Preferred amino acids to be substituted may include any amino acid with a large or bulky side chain, such as arginine (R), phenylalanine (F), tyrosine (Y), or tryptophan (W).

The CH3 domain is preferably derived from a human IgG1 antibody. Exemplary amino acid substitutions to the CH3 domain include T366Y, T366W, F405A, F405W, Y407T, Y407A, Y407V, T394S, and combinations thereof. A preferred exemplary combination is T366Y or T366W for the knob mutation on a first CH3 domain and Y407T or Y407V for the hole mutation on a second CH3 domain.

In certain embodiments of the invention, the two Fc domains of the antigen binding construct are heterodimerized through Fab arm exchange (FAE). A human IgG1 possessing a P228S hinge mutation may contain an F405L or K409R CH3 domain mutation. Mixing of the two antibodies with a reducing agent leads to FAE. This technology is described in U.S. Pat. No. 9,212,230 and Labrijn A. F., Proc Natl Acad Sci USA 110(13): 5145-5150 (2013).

In certain embodiments of the invention, the two Fc domains of the antigen binding construct are heterodimerized through electrostatic steering effects. This dimerization technique utilizes electrostatic steering to promote and strengthen Fc domain pairing in the CH3/CH3 domain interface. The charge complementarity between two CH3 domains is altered to favour heterodimerization (opposite charge pairing) over homodimerization (same charge pairing). In this method, the electrostatic repulsive forces prevent homodimerization. Exemplary amino acid residue substitutions may include K409D, K392D, and/or K370D in a first CH3 domain, and D399K, E356K, and/or E357K in a second CH3 domain. This technology is described in US Patent Application Publication No. 2014/0154254 A1 and Gunasekaran K., J Biol Chem 285(25): 19637-19646 (2010).

In certain embodiments of the invention, the two Fc domains of the antigen binding construct are heterodimerized through hydrophobic interaction effects. This dimerization technique utilizes hydrophobic interactions instead of electrostatic ones to promote and strengthen Fc domain pairing in the CH3/CH3 domain interface. Exemplary amino acid residue substitution may include K409W, K360E, Q347E, Y349S, and/or S354C in a first CH3 domain, and D399V, F405T, Q347R, E357W, and/or Y349C in a second CH3 domain. Preferred pairs of amino acid residue substitutions between a first CH3 domain and a second CH3 domain include K409W:D399V, K409W: F405T, K360E:Q347R, Y349S:E357W, and S354C:Y349C. This technology is described in US Patent Application Publication No. 2015/0307628 A1.

In certain embodiments of the invention, heterodimerization can be mediated through the use of leucine zipper fusions. Leucine zipper domains fused to the C terminus of each CH3 domain of the antibody chains force heterodimerization. This technology is described in Wranik B., J Biol Chem 287(52): 43331-43339 (2012).

In an aspect of the invention, heterodimerization can be mediated through the use of a Strand Exchange Engineered Domain (SEED) body. CH3 domains derived from an IgG and IgA format force heterodimerization. This technology is described in Muda M., Protein Eng. Des. Sel. 24(5): 447-454 (2011).

Unless otherwise stated, all antibody constant region numbering employed herein corresponds to the EU numbering scheme, as described in Edelman et al., Proc. Natl. Acad. Sci. USA 63(1): 78-85 (1969).

Additional methods of heterodimerization of heavy and/or light chains and the generation and purification of asymmetric antibodies are known in the art. See, for example, Klein C., mABs 4(6): 653-663 (2012), and U.S. Pat. No. 9,499,634, each of which is incorporated herein by reference.

D. Non-Heterodimerization Based Modification of the Fc Region

The antibody molecules of the invention may have one or more amino acid substitutions, insertions or deletions within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g., by addition or deletion of N- or O-linked glycosylation sites).

The bispecific antigen binding constructs of the invention may be modified within the Fc region to increase binding affinity for the neonatal Fc receptor (FcRn). The increased binding affinity may be measurable at acidic pH (for example from about approximately pH 5.5 to approximately pH 6.0). The increased binding affinity may also be measurable at neutral pH (for example from approximately pH 6.9 to approximately pH 7.4). By "increased binding affinity" is meant increased binding affinity to FcRn relative to the unmodified Fc region. Typically the unmodified Fc region will possess the wild-type amino acid sequence of human IgG1, IgG2, IgG3 or IgG4. In such embodiments, the increased FcRn binding affinity of the antibody molecule having the modified Fc region will be measured relative to the binding affinity of wild-type IgG1, IgG2, IgG3 or IgG4 for FcRn.

Several Fc substitutions have been reported to increase FcRn binding and thereby improve antibody pharmacokinetics. Such substitutions are reported in, for example, Zalevsky et al. (2010) Nat. Biotechnol. 28(2):157-9; Hinton et al. (2006) J Immunol. 176:346-356; Yeung et al. (2009) J Immunol. 182:7663-7671; Presta L G. (2008) Curr. Opin. Immunol. 20:460-470; and Vaccaro et al. (2005) Nat. Biotechnol. 23(10):1283-88, the contents of which are incorporated herein by reference in their entirety.

In certain embodiments, one or more of the antibody molecules of the bispecific antigen binding constructs described herein comprise a modified human IgG Fc domain comprising a modification comprising or consisting of the amino acid substitutions H433K and N434F, wherein the Fc domain numbering is in accordance with EU numbering. In a further certain embodiment, one or more of the antibody molecules of the combinations described herein comprise a modified human IgG Fc domain comprising a modification comprising or consisting of the amino acid substitutions M252Y, S254T, T256E, H433K and N434F, wherein the Fc domain numbering is in accordance with EU numbering.

The bispecific antigen binding constructs may also be modified so as to form immunoconjugates comprising an antibody conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension, as described by Chan and Carter (2010) Nature Reviews: Immunology 10:301-316, incorporated herein by reference.

In certain embodiments, the Fc region may be engineered such that it lacks effector function, e.g., lacks the ability to direct antibody-dependent cellular cytotoxicity (ADCC) or complement-dependent cytotoxicity (CDC). Such engineered effectorless Fc regions are referred to herein as "Fc dead." In certain embodiments, the bispecific antigen binding constructs of the invention may have an Fc region derived from naturally-occurring IgG isotypes having reduced effector function, for example IgG4. Fc regions derived from IgG4 may be further modified to increase therapeutic utility, for example by the introduction of modifications that minimise the exchange of arms between IgG4 molecules in vivo. Fc regions derived from IgG4 may be modified to include the S228P substitution.

In certain embodiments, the bispecific antigen binding constructs of the invention are modified with respect to glycosylation. For example, an aglycosylated antibody can be made (i.e., the antibody lacks glycosylation). Glycosylation can be altered, for example, to increase the affinity of the antibody for the target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. In certain embodiments, the Fc region may be engineered to reduce or eliminate glycosylation. For example, the N297 site in the CH2 domain may be mutated to reduce or eliminate glycosylation, wherein the Fc domain numbering is in accordance with EU numbering. In certain embodiments, the bispecific antigen binding constructs of the invention comprise one or more N297A mutations. The N297A mutation has been shown to reduce antibody-dependent cellular cytotoxicity (ADCC). See, for example, Borrok et al. (2012) ACS Chem Biol. 7(9):1596-1602.

E. Polynucleotides Encoding Multispecific Antigen Binding Constructs

The invention also provides polynucleotide molecules encoding the multispecific antigen binding constructs of the invention, as well as expression vectors containing nucleotide sequences which encode the multispecific antigen binding constructs of the invention operably linked to regulatory sequences which permit expression of the multispecific antigen binding construct polypeptides in a host cell or cell-free expression system. The invention also provides a host cell or cell-free expression system containing these expression vectors.

Polynucleotide molecules encoding the multispecific antigen binding constructs of the invention include, for example, recombinant DNA molecules. The terms "nucleic acid," "polynucleotide," and "polynucleotide molecule" as used herein are interchangeable and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated." This term, when applied to a nucleic acid molecule, refers to a nucleic acid molecule that is separated other components, including sequences with which it is immediately contiguous in the naturally occurring genome, of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of a multispecific antigen binding construct according to the invention, recombinant polynucleotide encoding the various construct components may be prepared (using standard molecular biology techniques) and inserted into a replicable vector for expression in a chosen host cell or in a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36: 59 (1977)); baby hamster kidney cells (BHK, ATCC CCL 10); Chinese hamster ovary cells/-DHFR (CHO, Urlaub et al., Proc. Natl. Acad. Sci. USA 77: 4216 (1980)); mouse Sertoli cells (TM4, Mather, Biol. Reprod. 23: 243-251 (1980)); mouse myeloma cells SP2/0-AG14 (ATCC CRL 1581; ATCC CRL 8287) or NSO (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383: 44-68 (1982)); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line. Whole human beings into which an expression vector encoding an antigen binding polypeptide according to the invention has been introduced are explicitly excluded from the definition of a "host cell".

F. Therapeutic Utility of Multispecific Antigen Binding Constructs

As used herein, the terms "treat," "treating," or "treatment" means slowing, interrupting, arresting, controlling, stopping, reducing severity of a symptom, disorder, condition or disease, but does not necessarily involve a total elimination of all disease-related symptoms, conditions or disorders.

For human therapeutic use the multispecific antigen binding constructs described herein may be administered to a human subject in need of treatment in an "effective amount". The term "effective amount" refers to an amount or dose of an agent which is sufficient to achieve a desired result. In certain embodiments, the term "effective amount" refers to an amount of dose of an agent which, upon single or multiple dose administration to a subject, provides therapeutic efficacy in the treatment of disease. In certain embodiments, the term "effective amount" refers to an amount of dose of an agent which, upon single or multiple dose administration to a human patient, provides therapeutic efficacy in the treatment of disease. For example, the term "effective amount" can refer to an amount or dose of a multispecific antigen binding construct of the invention which, upon single or multiple dose administration to a human patient having a disease, provides therapeutic efficacy in the treatment of the disease.

Therapeutically effective amounts of the multispecific antigen binding construct can comprise an amount in the range of from about 0.1 mg/kg body weight to about 20 mg/kg body weight per single dose. In certain embodiments, a therapeutically effective amount of the multispecific antigen binding construct can comprise an amount in the range of from about 1 mg/kg body weight to about 10 mg/kg body weight per single dose. A therapeutically effective amount for any individual patient can depend on factors such as the age and overall condition of the patient, as well as the nature and severity of the disease to be treated. A therapeutically effective amount for any individual patient can be determined by the healthcare professional by, for example, monitoring the effect of the antigen binding construct on a biomarker, such as cell surface expression of the target antigen in tumour tissues, or a symptom such as tumour regression, etc. The amount of antigen binding construct administered at any given time point may be varied so that optimal amounts of antigen binding construct, whether employed alone or in combination with any other therapeutic agent, are administered during the course of treatment.

It is also contemplated to administer the antigen binding constructs described herein, or pharmaceutical compositions comprising such constructs, in combination with any other treatment, as a combination therapy.

G. Pharmaceutical Compositions

The scope of the invention includes pharmaceutical compositions, containing an antigen binding construct of the invention, formulated with one or more pharmaceutically acceptable carriers or excipients. Techniques for formulating antigen binding constructs such as monoclonal antibodies for human therapeutic use are well known in the art and are reviewed, for example, in Wang et al., J Pharm Sci 96: 1-26 (2007).

The pharmaceutical composition can be formulated for administration by any suitable route of administration, including, without limitation, intravenous (i.v.), intraperitoneal (i.p.), intramuscular (i.m.), intratumoral, oral, other enteral, subcutaneous (s.c.), and pulmonary.

H. Purification of Multispecific Antigen Binding Constructs

The scope of the invention includes methods of purifying the multispecific antigen binding constructs of the invention. Methods of purification may include methods based on physicochemical fractionation. Such methods include size exclusion chromatography (SEC), ammonium sulphate precipitation, ion exchange chromatography (IEC), and immobilized metal chelate chromatography (IMAC). Methods of purification may include affinity purification. Such methods rely on Protein A, Protein G, and/or Protein L as affinity ligands to conserved regions of an antigen binding construct. The affinity ligands may be conjugated to a resin to facilitate purification. An additional affinity purification method may rely on specific binding to the IgG CH1 domain of an antibody. This is a CH1-selective chromatography method.

The multispecific binding constructs of the instant disclosure may be purified by SEC. The size of the multispecific binding constructs of the instant disclosure, comprising a VHH binding region and a Fab portion of a conventional IgG antibody (e.g., a SIMPLE antibody), each operatively linked to an Fc domain, are expected to be about 112 kDa. A conventional IgG antibody formed by the dimerization of two Fab portions, each operatively linked to an Fc domain, is expected to be about 150 kDa. A VHH antibody formed by the dimerization of two VHH portions, each operatively linked to an Fc domain, is expected to be about 75 kDa. Given the size difference between the desired multispecific binding constructs (~112 kDa) and the two possible undesired alternative binding constructs (~150 kDa and/or 75 kDa), one of skill in the art will readily appreciate that the desired multispecific antigen binding constructs may be readily purified from the undesired binding constructs by SEC.

Regardless of whether or not the resulting multispecific antigen binding construct has been stabilized by cross-linking, the method of the invention may, in some embodiments, comprise a further step of purifying the multispecific antigen binding construct. Mixtures containing multispecific antigen binding constructs can be purified using standard chromatography techniques, such as (but not limited to) standard Protein A chromatography, Protein G, Protein L, cationic/anionic exchange chromatography, size exclusion chromatography, hydrophobic interaction chromatography, thiophilic chromatography or using ligands designed to capture IgG molecules (Protein A mimetics, Llama VHH ligands and the like). Alternatively, the multispecific antigen binding constructs can be precipitated using standard techniques such as salt-induced precipitation (ammonium sulphate), addition of organic solvents (DMSO, ethanol), changing pH or non-ionic polymers (polyethylene glycol). In another setting, multispecific antigen binding constructs can be applied to filtration techniques using membranes allowing concentration of the multispecific antigen binding constructs. Combinations of all these techniques may be required to purify a multispecific antigen binding construct to full homogeneity as certain mixtures may still contain parent monospecific IgG molecules as well as the multispecific antigen binding construct. Additional purification steps may then be required to separate the multispecific antigen binding construct from the parent monospecific IgG molecules. This can be done by purification by binding and elution using an affinity column for the first binding specificity followed by binding and elution using an affinity column for the second binding specificity.

The quantity, quality, and purity of (purified) multispecific antigen binding constructs can be analyzed using routine biochemical techniques such as absorbance measurements, HP-SEC, SDS-PAGE, native PAGE and RP-HPLC. Additional techniques that can discriminate multispecific antigen binding constructs from the parent IgG molecules include, but are not limited to IEF, cIEF, CIEX, and mass spectrometry (ESI, MALDI), allowing highly accurate separation and detection of the molecules on the basis of charge and/or mass. Dual binding specificity of bispecific antigen binding constructs can be assessed using any of a variety of different binding assay formats using, for instance, ELISA, RIA, surface plasma resonance (SPR), Bio-layer Interferometry, DELFIA, FRET, ECL, Gyros, and AlfaScreen. Purification methods are described in U.S. Pat. No. 9,212,230.

INCORPORATION BY REFERENCE

Various patents, published patent applications, and publications are cited in the foregoing description and throughout the following examples, each of which is incorporated by reference herein in its entirety.

EXAMPLES

The invention will be further understood with reference to the following non-limiting examples.

Example 1—Generation and Purification of Anti-Target A/Anti-Target B Antigen Binding Construct Anti-Target A is a conventional antibody with binding specificity to Target A. Anti-Target A is able to neutralize the activation of Target A in murine CD4+ splenocytes. Anti-Target B is a VHH with binding specificity to Target B. A bispecific antigen binding construct of Anti-Target A and Anti-Target B for binding to Target A, Target B, or a Target A-Target B complex was generated using knob-into-hole (KIH) technology. Anti-Target B VHH was fused to mIgG2a_hole. Anti-Target A-VH was cloned as a mIgG2a_knob, and Anti-Target A-VL was cloned as CLVA.

Figure 5A:
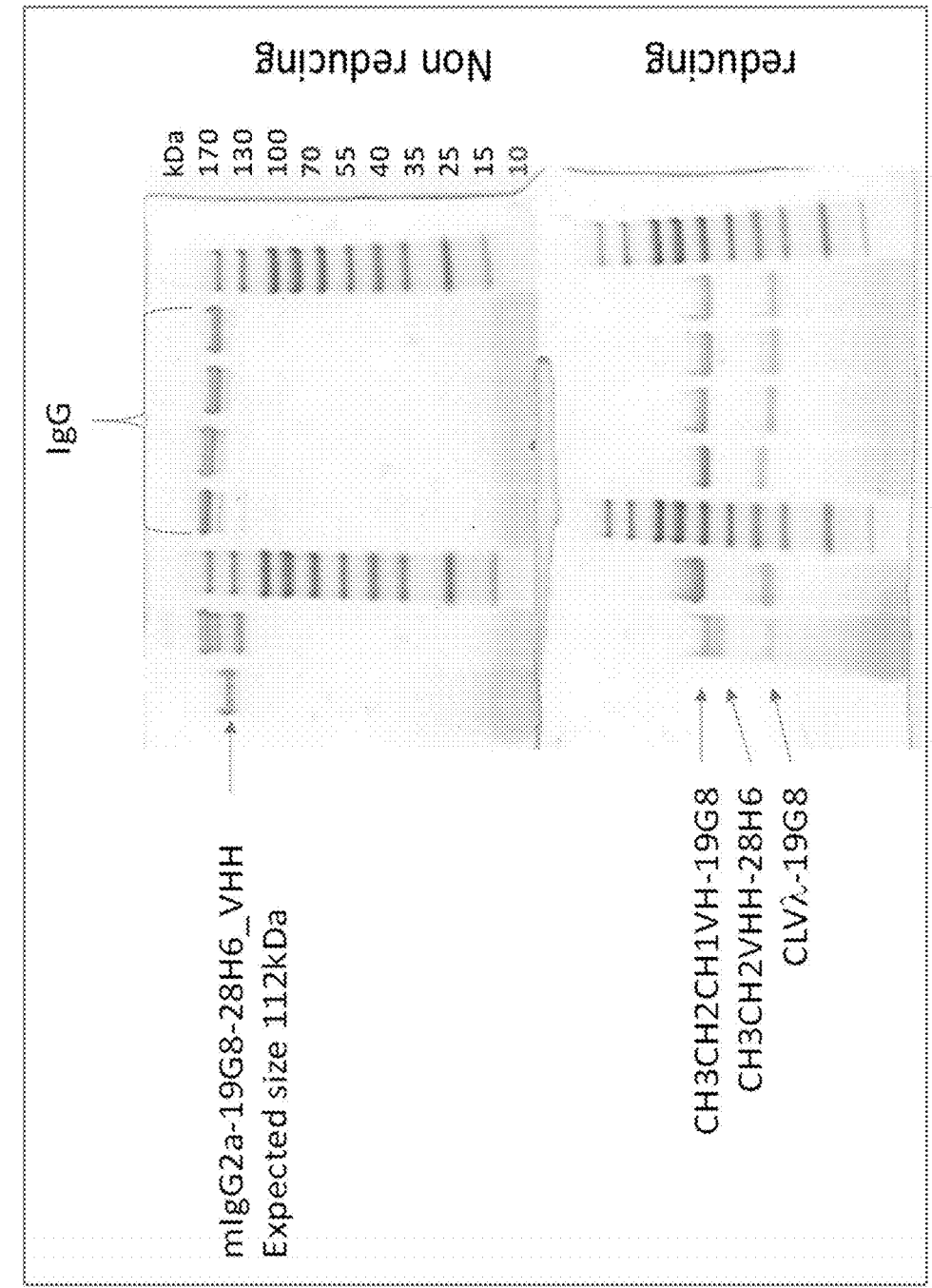
FIGS. 5A-5B depict a Coomassie Brilliant Blue stained SDS-PAGE of antigen binding constructs. Stained gels are shown of nonreduced samples and reduced samples.

For production of the Anti-Target A/Anti-Target B antigen binding construct 10×100 ml of 293E cells were transfected with 20 µg of each of the following constructs per 100 ml:

mFcFusionlgG2aKnob_Anti-Target B-VHH, mIgG2aHole_Anti-Target A_VH, and CLVA_Anti-Target A. The mIgG2aHole, mIgG2aKnob, mFcFusion IgG2aHole, and mFcFusionlgG2aKnob constructs were generated by KpnI-NotI cloning into pUPE (pCDNA3.1-like vector). Anti-Target A_VH was BsmBI cloned into the pUPE-mIgG2aHole vector. Anti-Target B-VHH was BsmBI cloned into the pUPE-mFcFusionlgG2aKnob vector. The sample was purified over protein A beads. Bound antigen binding construct was eluted and analysed using SDS-PAGE. FIG. 5A shows an SDS-PAGE gel stained with Coomassie blue, illustrating purification of the antigen binding construct at the correct size of 112 kDa. Note that the molecular weight marker migrated faster compared to the samples. The antigen binding construct had a lower band compared to full IgGs. Under a normal scenario, mispairings would result in the formation of a full IgG of 150 kDa, a VHH-Fc fusion of 75 kDa, and a bispecific format of about 112 kDa. However, FIG. 5A shows that only a 112 kDa product was produced, indicating that the desired bispecific format was preferentially produced. Under reducing conditions, a double band was seen for the two heavy chains. Note that the mFcFusionlgG2aKnob_Anti-Target B-VHH does not contain a CH1 domain and does not have a light chain, resulting in a product of about 37 kDa. The heavy chain of mIgG2aHole_Anti-Target A-VH is expected to be about 50 kDa. The light chain of Anti-Target A is about 25 kDa.

Accordingly, the bispecific format of the invention ensures that only the correct bispecific antibody is obtained. In particular, only the mIgG2aHole_Anti-Target A_VH construct pairs with the mFcFusionlgG2aKnob_Anti-Target B-VHH construct. The remaining light chain CLVA_Anti-Target A construct can only pair with the Anti-Target A_VH chain because a light chain is incapable of pairing with a VHH chain. It will be readily apparent to one of skill in the art that the instant invention is not limited to the above recited KIH heterodimerization method. Any appropriate heterodimerization method, such as described elsewhere herein, may be employed in the above-described bispecific antibody format.

Figure 7A:
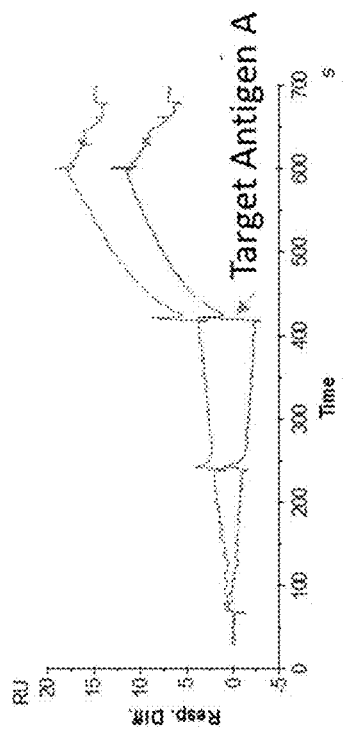
FIGS. 7A-7D depict binding affinity of the antigen binding construct as measured by Biacore (SPR) to (FIG. 7A) Immobilized Target Antigen B, (FIG. 7B) Immobilized Target A, (FIG. 7C) PBS, and (FIG. 7D) isotype control.
Figure 7B:
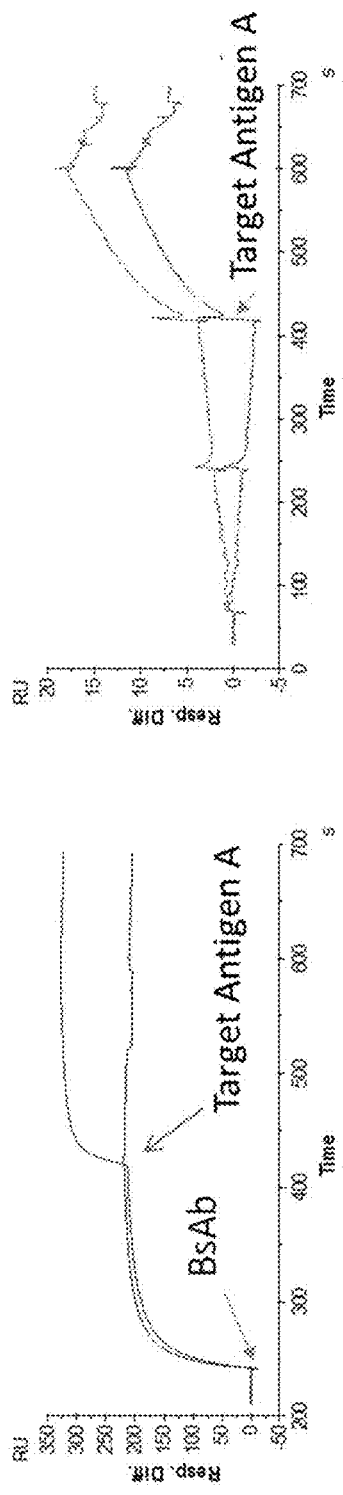
Figure 7C:
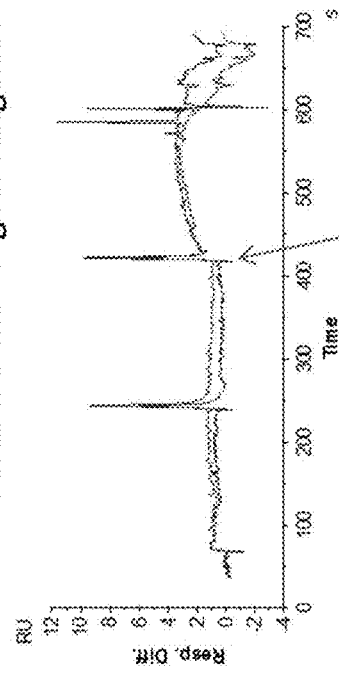
Figure 7D:
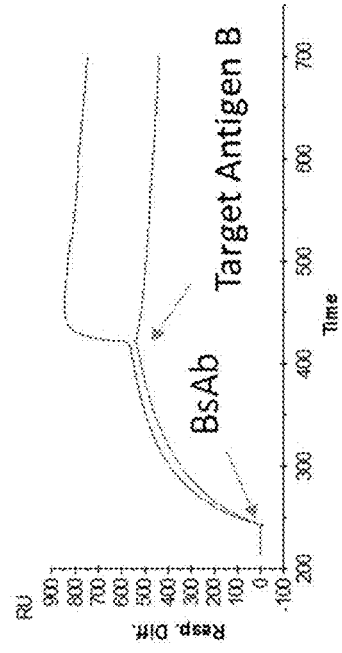

Example 2—Characterization of Anti-Target A/Anti-Target B Antigen Binding Construct The antigen binding construct of Example 1 was analysed on Biacore (SPR) for its binding characteristics to Target A and Target B. The construct was able to capture both Target A and Target B. (Compare FIGS. 7A and 7B with the PBS and isotype control of FIGS. 7C and 7D).

Figure 8A:
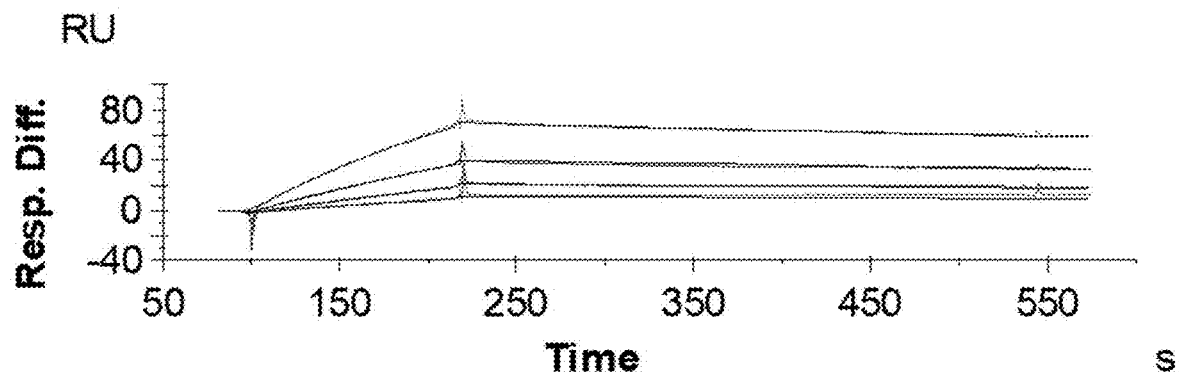
FIGS. 8A-8C depict binding kinetics of the antigen binding construct to (FIG. 8A) Target A, (FIG. 8B) Target B, and (FIG. 8C) Target A-Target B complex.
Figure 8B:
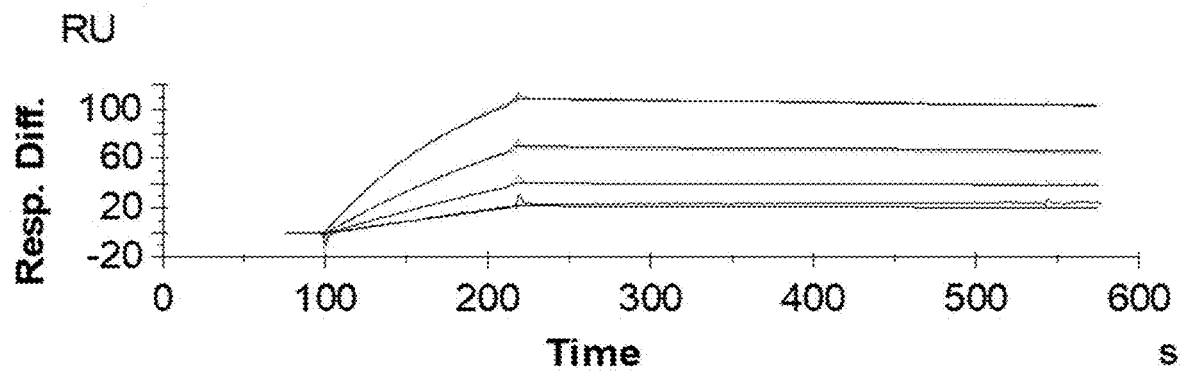
Figure 8C:
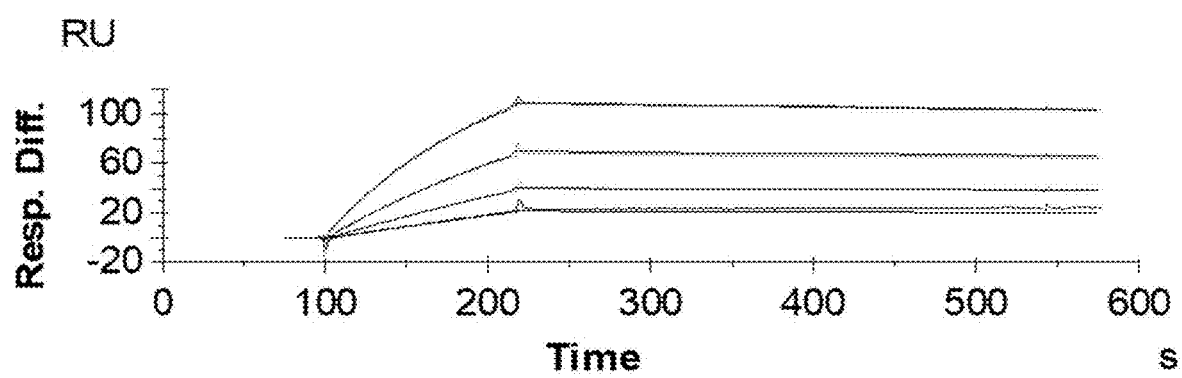

The affinity of the antigen binding construct for a Target A-Target B complex is much higher compared to the affinity for Target A or Target B, indicating bivalent binding (FIGS. 8A-8C and Table 5). Note that the detection limit of the Biacore is +1-1E-12, so the affinity indicated in FIG. 8 is an overestimation.

TABLE 5

Affinity Measurement of the Antigen Binding Construct to Target A-Target B complex, Target A, and Target B by Biacore.

| | $k_a$ (1/Ms) | $k_d$ (1/s) | KD (M) |
|---|---|---|---|
| Target A-Target B complex | 5.15E+05 | 4.22E-08 | 8.20E-14 |
| Target A | 2.16E+05 | 5.05E-04 | 2.34E-09 |
| Target B | 4.86E+05 | 1.42E-04 | 2.93E-10 |

It is possible that the bivalent interaction of the antigen binding construct, demonstrated in FIGS. 8A-8C and Table 5, is a result of the antigen binding construct binding to the Target B of one complex and the Target A of a neighbouring complex, rather than binding to Target B and Target A within the same complex molecule. To determine whether the antigen binding construct binds within the same complex molecule, a Biacore CM5 chip was coated with the antigen binding construct. Target A-Target B complex, Target A, and Target B were allowed to bind the chip (Table 6). The affinity to Target B is similar to what is shown when Target B is immobilized and the antigen binding construct is allowed to bind. Target A bound with relatively high affinity to the immobilized antigen binding construct because Target A is a dimer. This allows a bivalent interaction of Target A with the antigen binding construct-coated chip. The fact that the affinity of the complex to the immobilized antigen binding construct is clearly higher than the affinity of Target B to the immobilized antigen binding construct suggests that the antigen binding construct binds within one complex molecule.

TABLE 6

Affinity Measurement of Target A-Target B complex, Target A, and Target B by Biacore.

| | KD (M) |
|---|---|
| Target A-Target B complex | 1.25E-12 |
| Target A | 8.04E-11 |
| Target B | 1.14E-10 |

Example 3—Generation and Purification of Target C/Target D Antigen Binding Construct VHH2H3 and VHH3H2 are different VHH antibodies with binding specificity to Target D. 4R36B7 is a conventional antibody with binding specificity to Target C. A bispecific antigen binding construct of VHH2H3 or VHH3H2 and 4R36B7 for binding to Target C and Target D was generated using knob-into-hole (KIH) technology. VHH2H3 and VHH3H2 were fused to mIgG2a_hole. 4R36B7-VH was cloned as a mIgG2a_knob, and 4R36B7-VL was cloned as CLVA.

Figure 5B:
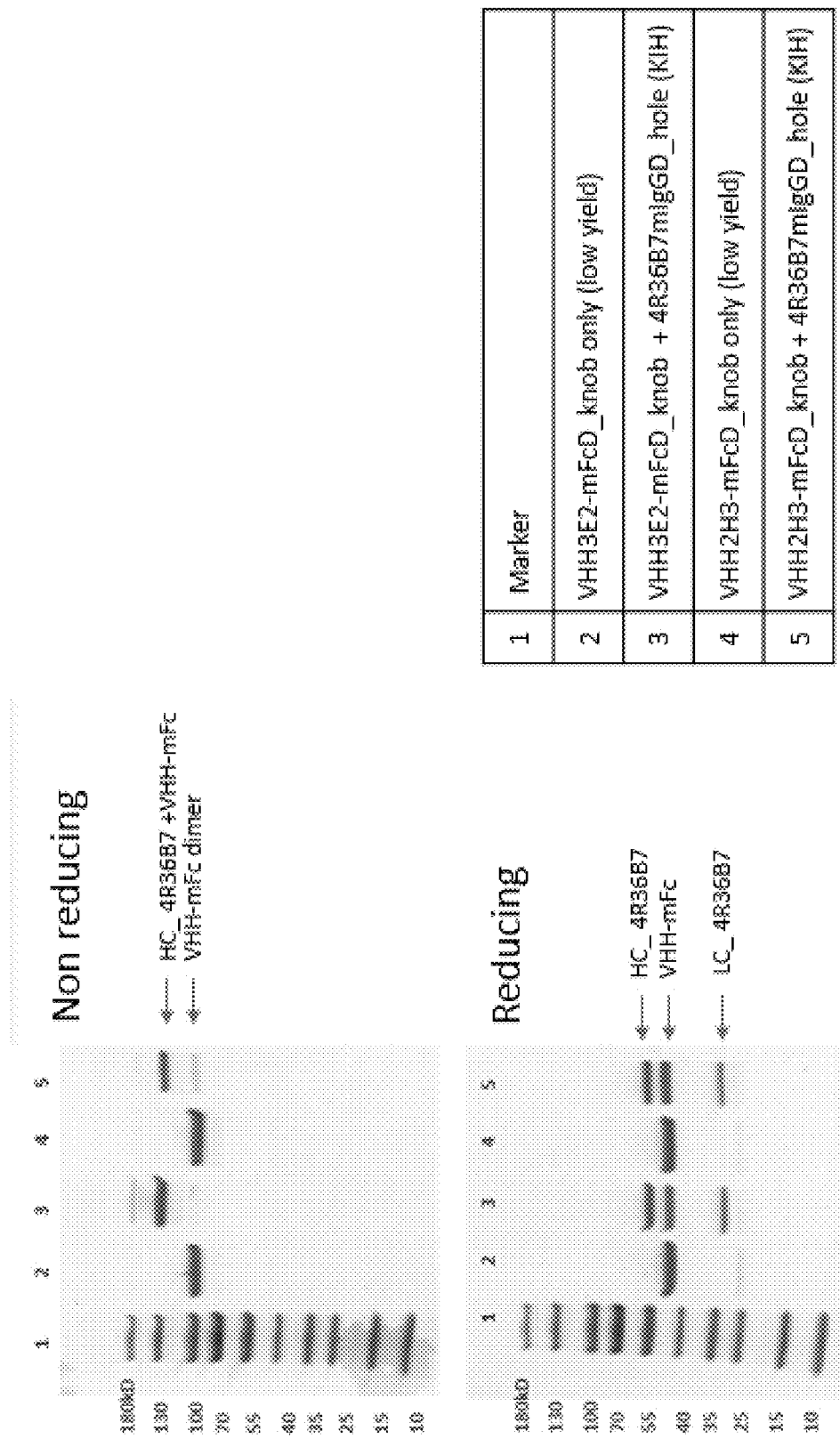

The Target C/Target D antigen binding construct were produced in 293E cells The sample was purified over protein A beads. Bound antigen binding construct was eluted and analysed using SDS-PAGE. FIG. 5B shows an SDS-PAGE gel stained with Coomassie blue, illustrating purification of the antigen binding construct at the correct size of approximately 120 kDa. Note that the molecular weight marker migrated faster compared to the samples. The antigen binding construct has a lower band compared to full IgGs. Under a normal scenario, mispairings would result in the formation of a full IgG of 150 kDa, a VHH-Fc fusion of 75 kDa, and a bispecific format of about 120 kDa. However, FIG. 5B shows that only a 120 kDa product was produced, indicating the that the desired bispecific format was preferentially produced.

Accordingly, the bispecific format of the invention ensures that only the correct bispecific antibody was obtained. In particular, only the 4R36B7 mIgG2a Fc dead_Knob construct pairs with the VHH2H3-mFc dead_Hole or VHH3H2-mFc dead_Hole construct. The remaining light chain CLVA_4 R36B7 construct can only pair with the 4R36B7 mIgG2a Fc dead heavy chain because a light chain is incapable of pairing with a VHH chain. It will be readily apparent to one of skill in the art that the instant invention is not limited to the above recited KIH heterodimerization method. Any appropriate heterodimerization method, such as describe elsewhere herein, may be employed in the above described bispecific antibody format.

Example 4—Size Exclusion Chromatography (SEC) of Antigen Binding Construct

The chromatographic system used was an Agilent 1260 Infinity II, equipped with a quaternary pump, automatic injector, refrigerated autosampler (6° C.), on-line degasser and a DAD detector. The column was a Waters XBridge BEH 200 Å SEC (3.5 μm, 7.8×300 mm; Waters, Cat No 176003596) coupled to a Waters XBridge BEH 200 Å SEC pre-guard column (3.5 μm, 7.8×30 mm; Waters, Cat No176003591). The column was first equilibrated with mobile phase for 10 column volumes (CV), and it was not kept in a thermostated compartment. The operational flow rate was set to 1 mL/min for 30 min while using PBS as mobile phase (Sigma, Cat D8537). The detector was set to wavelengths 280 and 214 nm simultaneously (reference wavelength at 360 nm with a cut-off of 100 nm). Aggregation monitoring was followed on channel 214 nm in the presence of a high aggregation control sample (HAC) known to have 3.5% aggregates. A sample monitored at several occasions in the process was taken along as a QC sample. Data acquisition was done with the Chemstation Openlab CDC software (Agilent).

Figure 6A:
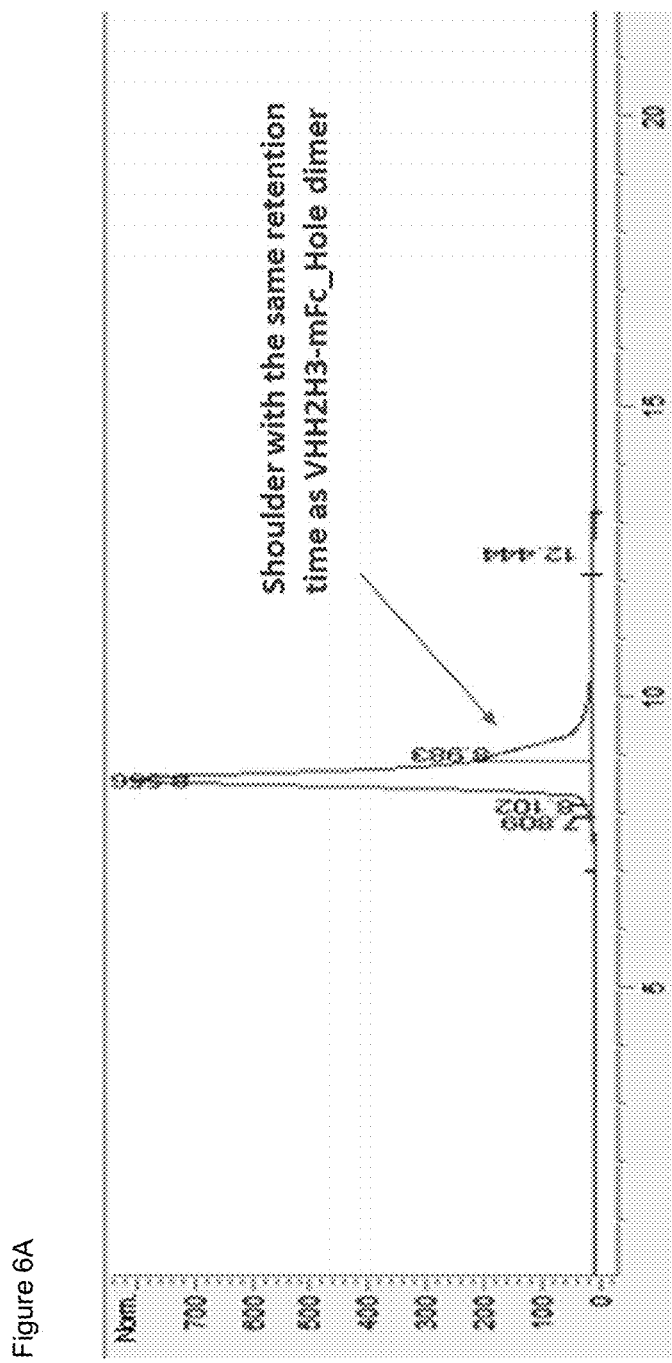
FIGS. 6A-6C depict size exclusion chromatography (SEC) data of the antigen binding constructs VHH2H3-mFc_Hole+4R36B7mIgG_Knob, VHH3H2-mFc_Hole+4R36B7mIgG_Knob, and VHH3H2-mFc_Hole only, respectively.
Figure 6B:
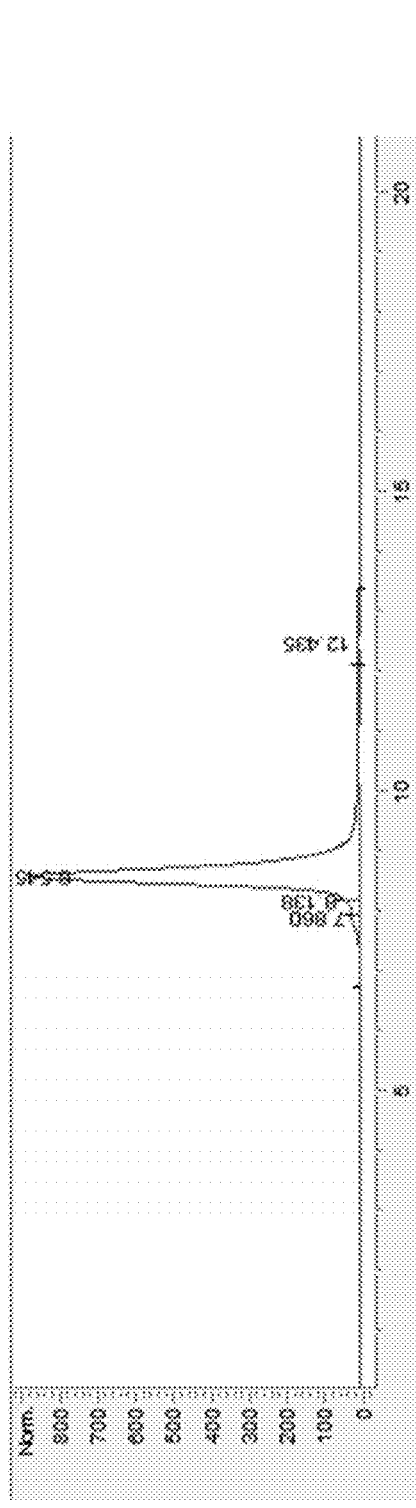
Figure 6C:
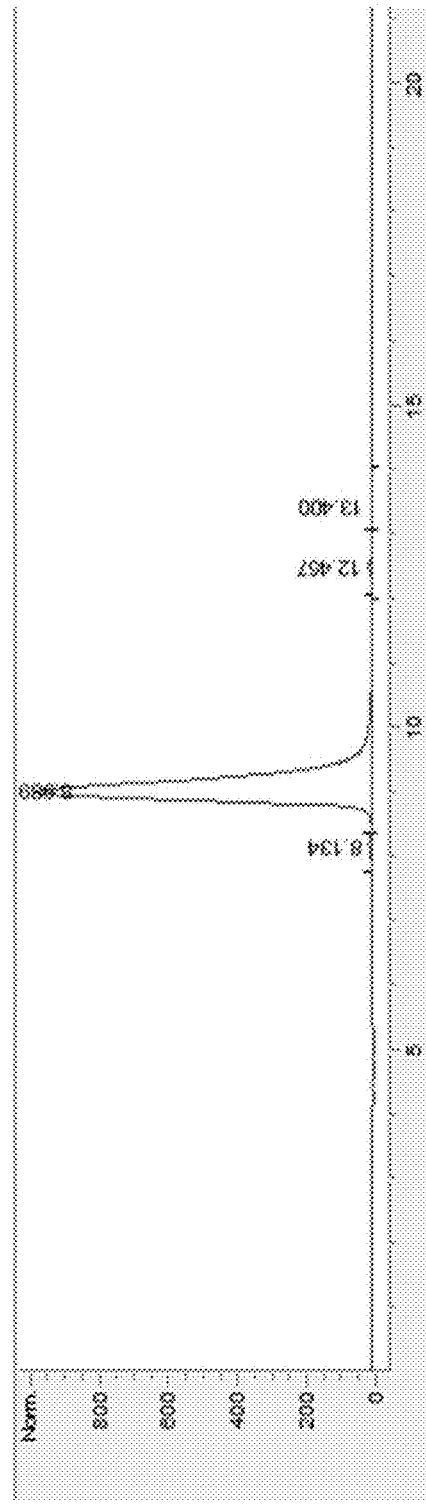

FIGS. 6A-6C and Table 7 below show the results of the SEC analysis for the Target C/Target D bispecific antibodies.

TABLE 7

SEC results for the Target C/Target D antibodies.

| Sample (20 μg load) | Elution Time (min) | % Monomer | % Aggregation |
|---|---|---|---|
| mu36B7-IgG | 8.166 | 99.8 | 0.2 |
| 5MP95G7-mIgG | 8.106 | 99.8 | 0.2 |
| VHH2H3-mFc_Hole + 4R36B7mIgG_Knob (KIH) | 8.556 | ≥99.5 | ≤0.5 |
| VHH3E2-mFc Hole + 4R36B7mIgG_Knob (KIH) | 8.545 | 97.9 | 2.1 |
| VHH3E2-mFc_Hole only | 8.989 | 98.7 | 1.3 |

Example 5—Characterization of Target C/Target D Antigen Binding Construct

The affinity of the Target C/Target D binding constructs were measured with a Biacore 3000. A CM5 chip coated with around 500 RU of Target C or Target D using NHS chemistry as recommended was performed. A concentration range of the antibodies were added to the chip (9 concentrations, starting at 10 ug/ml). The molecular weight used was as follows: mIgG~150 kDa; mIgG-VHH-Fc~120 kDa; VHH-Fc dimer~80 kDa. The affinity was determined by fitting of the kinetic parameters with a 1:1 Langmuir binding model using the BiaEvaluation software. The results are depicted below in Table 8. Both antibody arms were found to be functional.

TABLE 8

Affinity Measurement of Target C and Target D by Biacore.

| Antibody | Range (nM) | Fitting | Coating Target C (500RU) | | | Coating Target D (500RU) | | |
|---|---|---|---|---|---|---|---|---|
| | | | Rmax at Cmax | KD (M) | Chi$^2$ | Rmax at Cmax | KD (M) | Chi$^2$ |
| 5MPm95G7-mIgGD (control anti-mIL-5) | 66.7 ± 0.01 | Local | NB | NB | — | 109 | 7.7E−10 | 1.7 |
| 4R36B7-mIgGD | 66.7 ± 0.01 | Local | 186 | 1.6E−10 | 3.9 | NB | NB | — |
| VHH2H3-mFcD_Hole + 4R36B7mIgGD_Knob (KIH) | 80 ± 0.01 | Local | 254 | 2.8E−10 | 0.9 | 186 | 9.6E−10 | 3.2 |
| VHH2H3-mFcD_Hole only | 117 ± 0.02 | Local | NB | NB | — | 193 | 3.0E−10 | 3.5 |
| VHH3E2-mFc_Hole + 4R36B7mIgGD_Knob (KIH) | 80 ± 0.01 | Local | 232 | 3.5E−10 | 0.6 | 67 | 3.6E−08 | 2.1 |
| VHH3E2-mFcD_Hole only | 117 ± 0.02 | Local | NB | NB | — | 190 | 8.5E−10 | 1.5 |

"NB" means no binding.

What is claimed is:

1. A bispecific antigen binding construct comprising
(a) a single VHH domain of a heavy-chain-only antibody (VHH antibody) which binds a first target antigen, wherein said VHH domain is fused to the N-terminus of a first human $IgG_1$ Fc domain polypeptide; and
(b) a single Fab portion of a conventional IgG antibody which binds a second target antigen, wherein said Fab portion is fused to the N-terminus of a second human $IgG_1$ Fc domain polypeptide;

wherein the first and second $IgG_1$ Fc domain polypeptides dimerize by knobs-into-holes interactions to form the bispecific antigen binding construct, and wherein the first human $IgG_1$ Fc domain polypeptide comprises tryptophan at EU position 366, and the second human $IgG_1$ Fc domain polypeptide comprises serine, alanine, and valine at EU positions 366, 368, and 407, respectively; or the second human $IgG_1$ Fc domain polypeptide comprises tryptophan at EU position 366, and the first human $IgG_1$ Fc domain polypeptide comprises serine, alanine, and valine at EU positions 366, 368, and 407, respectively.

2. A pharmaceutical composition comprising the bispecific antigen binding construct of claim 1.

3. The bispecific antigen binding construct of claim 1, wherein the conventional IgG antibody is obtained by immunization of an animal of the Camelidae family with the second target antigen.

4. The bispecific antigen binding construct of claim 1, wherein the bispecific antigen binding construct has a molecular weight in the range of from about 100 kDa to about 120 kDa.

* * * * *

UNITED STATES PATENT AND TRADEMARK OFFICE
CERTIFICATE OF CORRECTION

PATENT NO. : 12,071,486 B2  
APPLICATION NO. : 16/230326  
DATED : August 27, 2024  
INVENTOR(S) : Sebastian van der Woning et al.

Page 1 of 1

It is certified that error appears in the above-identified patent and that said Letters Patent is hereby corrected as shown below:

On the Title Page

Item (12) delete "Van Der Woning" and insert -- van der Woning et al. --

Item (72) 1st named Inventor "Sebastian Van Der Woning" should be "Sebastian van der Woning"

Signed and Sealed this
Eleventh Day of March, 2025

Coke Morgan Stewart
*Acting Director of the United States Patent and Trademark Office*